United States Patent [19]

Sheppard et al.

[11] Patent Number: 5,104,967
[45] Date of Patent: Apr. 14, 1992

[54] AMIDEIMIDE OLIGOMERS AND BLENDS

[75] Inventors: Clyde H. Sheppard, Bellevue, Wash.; Hyman R. Lubowitz, Rolling Hills Estates, Calif.

[73] Assignee: The Boeing Company, Seattle, Wash.

[21] Appl. No.: 181,013

[22] Filed: Apr. 13, 1988

Related U.S. Application Data

[63] Continuation-in-part of Ser. No. 92,740, Sep. 3, 1987, abandoned.

[51] Int. Cl.[5] ............................................. C08G 73/14
[52] U.S. Cl. ...................... 528/322; 528/125; 528/126; 528/128; 528/170; 528/171; 528/172; 528/173; 528/175; 528/176; 528/179; 528/187; 528/188; 528/207; 528/208; 528/223; 528/226; 528/229; 528/350; 528/351; 528/353; 526/262; 526/263; 526/285
[58] Field of Search .............. 528/125, 126, 322, 173, 528/170, 175, 128, 176, 172, 179, 183, 187, 188, 226, 207–208, 229, 350–353; 526/262, 263, 385; 560/48, 47; 505/432

[56] References Cited

U.S. PATENT DOCUMENTS

| | | | |
|---|---|---|---|
| 3,105,839 | 10/1963 | Renner | 528/361 |
| 3,485,867 | 12/1969 | Jackson | 560/3 |
| 3,659,007 | 4/1972 | Giambra | 560/3 |
| 3,781,249 | 12/1973 | Lubowitz et al. | 528/125 |
| 4,058,663 | 11/1977 | Black | 560/3 |
| 4,158,731 | 6/1979 | Baumann et al. | 528/322 |
| 4,251,417 | 2/1981 | Chow et al. | 528/125 |
| 4,251,420 | 2/1981 | Antonoplos et al. | 528/125 |
| 4,381,363 | 4/1983 | Reinhart, Jr. | 528/125 |
| 4,418,181 | 11/1983 | Monacelli | 528/125 |
| 4,536,559 | 8/1985 | Lubowitz et al. | 528/170 |
| 4,604,437 | 8/1986 | Renner | 528/322 |

FOREIGN PATENT DOCUMENTS 0289798 11/1988 European Pat. Off. .

OTHER PUBLICATIONS

Chemical Abstracts, Abstract No. 39809y, vol. 97, No. 6, Aug. 9, 1982, p. 30.

*Primary Examiner*—John Kight, III
*Assistant Examiner*—P. Hampton-Hightower
*Attorney, Agent, or Firm*—Seninger, Powers, Leavitt & Roedel

[57] ABSTRACT

The solvent-resistance and thermal stability of polyamideimides of the general formulae:

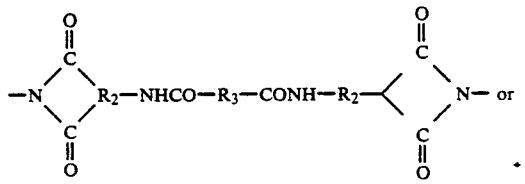

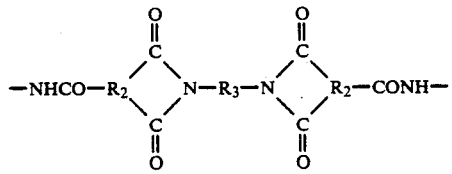

is improved by capping the amideimides with a cross-linking functionality (Y) containing a residue selected from the group of:

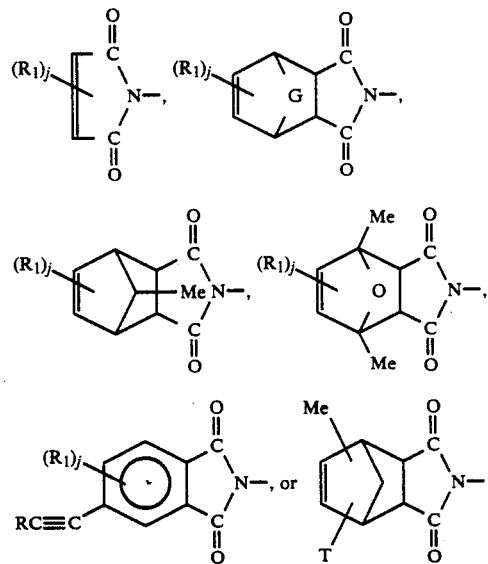

wherein
$R_1$ = lower alkyl, lower alkoxy, aryl, aryloxy, substituted alkyl, substituted aryl (either including hydroxyl or halo-substituents), halogen, or mixtures thereof;
j = 0, 1, or 2;
G = —$CH_2$—, —O—, —S—, —$SO_2$—, —SO—, —CO—, —CHR—, or —$CR_2$—;
R = hydrogen, lower alkyl, or phenyl;
T = methallyl or allyl;
Me = methyl;
$R_2$ = a trivalent organic radical; and
$R_3$ = a divalent organic radical.

The amideimide oligomers may be linear or multidimensional, and can be processed into blends, prepregs, or composites. Methods of making these amideimides and intermediates useful in the syntheses are also described.

38 Claims, No Drawings

1

AMIDEIMIDE OLIGOMERS AND BLENDS

REFERENCE TO RELATED APPLICATIONS

The present application is a continuation-in-part application based upon U.S. patent application Ser. No. 092,740, filed Sep. 3, 1987, now abandoned.

TECHNICAL FIELD

The present invention relates to linear and multidimensional polyamideimide oligomers and blends that are solvent resistant, thermally stable, and easily processed into prepregs and composites. The resulting composites are useful for aerospace applications.

BACKGROUND OF THE INVENTION

Recently, chemists have sought to synthesize oligomers for high performance advanced composites suitable for aerospace applications. These composites should exhibit solvent resistance, be strong, tough, and impact resistant; be easy to process; and be thermoplastic. Oligomers and composites that have thermo-oxidative stability, and, accordingly, can be used at elevated temperatures are particularly desirable.

While epoxy-based composites are suitable for many applications, their brittle nature and susceptibility to degradation make them inadequate for many aerospace applications, especially those applications which require thermally stable, tough composites. Accordingly, research has recently focused on polyimide composites to achieve an acceptable balance between thermal stability, solvent resistance, and toughness. Still the maximum temperatures for use of the polyimide composites, such as PMR-15, are about 600°-625° F., since they have glass transition temperatures of about 690° F. PMR-15, however, suffers from brittleness.

There has been a progression of polyimide sulfone compounds synthesized to provide unique properties or combinations of properties. For example, Kwiatkowski and Brode synthesized maleic-capped linear polyarylimides as disclosed in U.S. Pat. No. 3,839,287. Holub and Evans synthesized maleic- or nadic-capped, imido-substituted polyester compositions as disclosed in U.S. Pat. No. 3,729,446. We synthesized thermally stable polysulfone oligomers as disclosed in U.S. Pat. No. 4,476,184 or U.S. Pat. No. 4,536,559, and have continued to make advances with polyetherimidesulfones, polybenzoxazolesulfones, polybutadienesulfones, and "star" or "star-burst" multidimensional oligomers. We have shown surprisingly high glass transition temperatures yet reasonable ease of processing and desirable physical properties in many of these oligomers and their composites.

Polybenzoxazoles, such as those disclosed in our copending applications U.S. Ser. No. 07/116,592 filed Nov. 3, 1987 now U.S. Pat. No. 4,965,336 (to Lubowitz & Sheppard) and Ser. No. 07/121,964 filed Nov. 17, 1987 U.S. Pat. No. 4,868,270 (to Lubowitz, Sheppard, and Stephenson), may be used at temperatures up to about 750°-775° F., since these composites have glass transition temperatures of about 840° F. Some aerospace applications need composites which have even higher use temperatures while maintaining toughness, solvent resistance, ease of processing, formability, strength, and impact resistance.

Multidimensional oligomers, such as disclosed in our copending applications U.S. Ser. Nos. 06/810,817 abandoned and 07/000,605, filed Jan. 5, 1987 have superior processing ease than some advanced composite oligomers since they can be handled at lower temperatures. Upon curing, however, the phenylimide end caps crosslink so that the thermal resistance of the resulting composite is markedly increased with only a minor loss of stiffness, matrix stress transfer (impact resistance), toughness, elasticity, and other mechanical properties. Glass transition temperatures above 950° F. are achievable.

Commercial polyesters, when combined with well-known diluents, such as styrene, do not exhibit satisfactory thermal and oxidative resistance to be useful for aircraft or aerospace applications. Polyarylesters are often unsatisfactory, also, since the resins often are semicrystalline which may makes them insoluble in laminating solvents, intractable in fusion, and subject to shrinking or warping during composite fabrication. Those polyarylesters that are soluble in conventional laminating solvents remain so in composite form, thereby limiting their usefulness in structural composites. The high concentration of ester groups contributes to resin strength and tenacity, but also makes the resin susceptible to the damaging effects of water absorption. High moisture absorption by commercial polyesters can lead to distortion of the composite when it is loaded at elevated temperature.

High performance, aerospace, polyester advanced composites, however, can be prepared using crosslinkable, end capped polyesterimide ethersulfone oligomers that have an acceptable combination of solvent resistance, toughness, impact resistance, strength, ease of processing, formability, and thermal resistance. By including Schiff base (—CH=N—), imidazole, thiazole, or oxazole linkages in the oligomer chain, the linear, advanced composites formed with polyester oligomers of our copending application U.S. Ser. No. 726,259 abandoned can have semiconductive or conductive properties when appropriately doped.

Conductive and semiconductive plastics have been extensively studied (see, e.g., U.S. Pat. Nos. 4,375,427; 4,338,222; 3,966,987; 4,344,869; and 4,344,870), but these polymers do not possess the blend of properties which are essential for aerospace applications. That is, the conductive polymers do not possess the blend of (1) toughness, (2) stiffness, (3) elasticity, (4) ease of processing, (5) impact resistance (and other matrix stress transfer capabilities), (6) retention of properties over a broad range of temperatures, and (7) high temperature resistance that is desirable in aerospace advanced composites. The prior art composites are often too brittle.

Thermally stable multidimensional oligomers having semiconductive or conductive properties when doped with suitable dopants are also known and are described in our copending applications (including U.S. Ser. No. 06/773,381 filed Sep. 5, 1985, now abandoned to Lubowitz, Sheppard and Torre). The linear arms of the oligomers contain conductive linkages, such as Schiff base (—N=CH—) linkages, between aromatic groups. Sulfone and ether linkages are interspersed in the arms. Each arm is terminated with a mono- or difunctional end cap (i.e. an end cap having one or two crosslinking functionalities) to allow controlled crosslinking upon heat-induced or chemically-induced curing. Other "semiconductive" oligomers are described in our other copending applications.

Polyamide oligomers and blends are described in our copending applications U.S. Ser. No. 07/046,202 filed May 4, 1987, U.S. Pat. No. 4,935,523; Ser. No. 07/051,884 filed May 18, 1987, U.S. Pat. No. 4,847,333 and Ser. No. 07/061,938, filed Jun. 12, 1987, U.S. Pat. No. 4,876,328 and polyetherimide oligomers and blends are described in our copending application U.S. Ser. No. 07/016,703 filed Feb. 20, 1987, U.S. Pat. No. 4,851,495.

Polyamideimides are generally injection-moldable, amorphous, engineering thermoplastics which absorb water (swell) when subjected to humid environments or when immersed in water. Polyamideimides are generally described in the following patents: U.S. Pat. Nos. 3,658,938; 4,628,079; 4,599,383; 4,574,144; or 3,988,344. The thermal integrity and solvent-resistance can be greatly enhanced by capping amideimide backbones with monomers that present one or two crosslinking functionalities at each end of the oligomer, as will be described.

Advanced composite blends, as we use that term, contain a blend of at least one oligomer from one chemical family and at least one polymer from a different chemical family. These advanced composite blends yield composites that possess properties intermediate to the properties of composites made from either pure component. For example, a polybenzoxazole oligomer can be blended with a polyethersulfone polymer to improve the flexibility (reduce the stiffness) of the resulting composite without significant reduction of the other, desired, high performance properties of the heterocycle (i.e. oxazole). We described these advanced composite blends in U.S. Ser. No. 07/116,592 filed Nov. 3, 1987, U.S. Pat. No. 4,965,336 and U.S. Ser. No. 07/121,964, filed Nov. 17, 1987, U.S. Pat. No. 4,868,270.

SUMMARY OF THE INVENTION

Solvent-resistant, linear or multidimensional polyamideimides include mono- or difunctional crosslinking end caps (i.e. caps having one or two crosslinking functionalities), and are generally prepared by condensing suitable diacid halides (i.e. dibasic carboxylic acid halides), diamines, and end caps. One or both of the diacid halides or diamines includes imide linkages. Alternatively, the oligomers can be prepared by condensing suitable dianhydrides, diamines, and end caps.

The improved properties are primarily attributable to the end caps which include hydrocarbon unsaturation, such as a residue (Y) selected from the group consisting of:

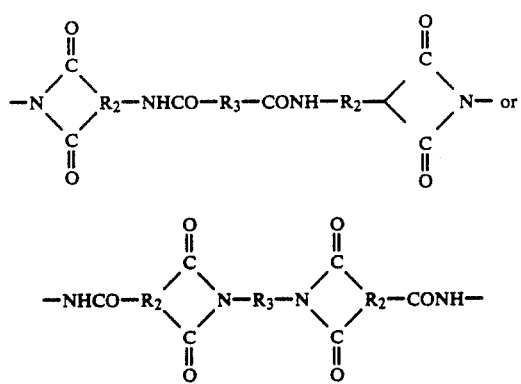

wherein
$R_1$ = lower alkyl, lower alkoxy, aryl, aryloxy, substituted alkyl, substituted aryl (either including hydroxyl or halo-substituents), halogen, or mixtures thereof;
$j$ = 0, 1, or 2;
$G$ = $-CH_2-$, $-O-$, $-S-$, $-SO_2-$, $-SO-$, $-CHR-$, $-CO-$, or $-CR_2-$;
$R$ = hydrogen, lower alkyl, or phenyl;
$T$ = methallyl or allyl; and
$Me$ = methyl.

The selection of a suitable end cap usually is made on the basis of thermal stability and thermal activation of the end cap so that the resin will soften near the activation temperature (i.e. the temperature at which a reverse Diels-Alder decomposition occurs for the norborene and other bridge compounds).

The amideimdes of the present invention generally include linkages of the following general nature along the backbone:

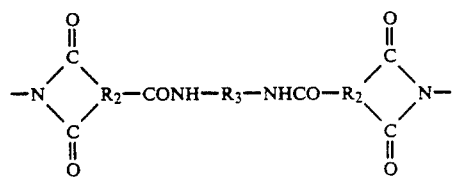

wherein
$R_3$ = an aromatic, aliphatic, or alicyclic radical, and preferably a phenoxyphenyl sulfone; and
$R_2$ = a trivalent organic radical, and preferably phenyl.

This linkage can be prepared, for example, by condensing 2 moles of an acid halide anhydride of the general formula:

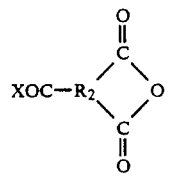

with a diamine of the formula: $H_2N-R_3-NH_2$. The linkage is characterized by a plane of symmetry about the $R_3$ residue.

The corresponding amideimide of the general formula:

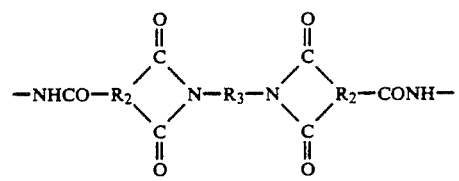

can be prepared if the acid anhydride:

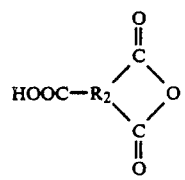

is used instead of the acid halide anhydride.

A sequential or homogeneous reaction scheme can be used to condense the reactants with sequential synthesis preferred to avoid side reactions. That is, the dianhydride or diacid halide can be prepared by the condensation of a diamine with the acid anhydride or acid halide anhydride followed by addition of more diamines and the end caps to complete the synthesis.

The homogeneous reaction scheme requires n moles of the acid anhydride or acid halide anhydride, n moles of the diamine, and 2 moles of the end cap of the general formula:

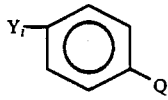

wherein Y is as previously defined;
n = a small integer, generally from 1–5;
i = 1 or 2; and
Q = —COX or —NH$_2$ Prepregs and cured composites can be readily prepared from the oligomers. For example, the oligomers can be applied to a compatible fiber cloth reinforcement, and the resulting prepreg can be cured in a vacuum bag process to form solvent-resistant advanced composites useful in aerospace applications.

Blends can also be prepared, and can be processed into prepregs or composites. The blends comprise mixtures of the crosslinking oligomers and a polymer that is incapable of crosslinking. Generally the blend comprises a substantially equimolar mixture of an amideimide oligomer and an amideimide polymer of substantially the same backbone and average formula weight having a quenching end cap of aniline or benzoic acid halide. The blend, however, might be an "advanced composite blend" and could include, for example, an imide, an amide, or both. Blends generally provide improved impact resistance over the corresponding pure oligomer without significant loss of solvent-resistance.

While the invention is mainly addressed to linear polyamideimide oligomers, multidimensional amideimides can also be prepared by reacting an amine or acid halide hub with the acid anhydrides, acid halide anhydrides, diamines, and end caps, as will be explained. For example, triaminobenzene can be reacted with

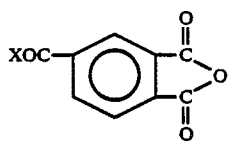

and an imidophenyl amine end cap to form a multidimensional amideimide.

Blended multidimensional amideimides can also be prepared.

In another aspect, the present invention relates to intermediates (or conjugates) that are useful for synthesizing linear or multidimensional polyamideimide oligomers. The intermediates can be grouped into two classes, namely, extended end caps or extended hubs. The extended end caps include compounds of the formulae:

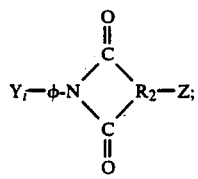

Y$_i$—φ-CONH—R$_3$—NH$_2$; and

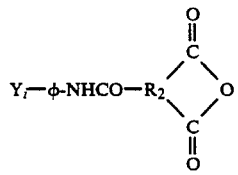

wherein
φ = phenyl;
i = 1 or 2;
R$_2$ = a trivalent organic radical;
Y =

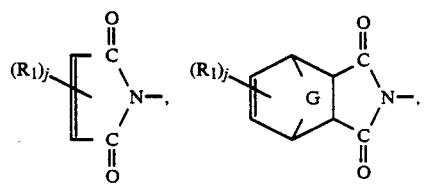

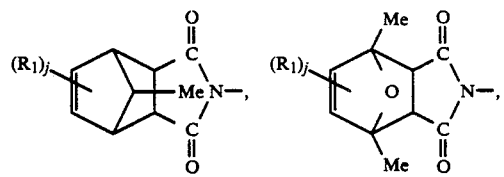

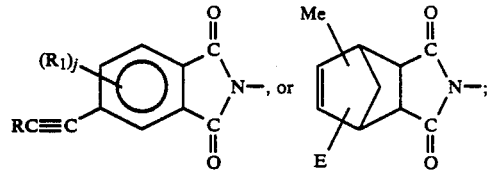

Z = —COOH or —COX;
X = halogen;
R$_3$ = a divalent organic radical;
R$_1$ = lower alkyl, lower alkoxy, aryl, aryloxy, substituted alkyl, substituted aryl, halogen, or mixtures thereof;
j = 0, 1, or 2;
G = —CH$_2$—, —O—, —S—, —SO$_2$—, —SO—, —CO—, —CHR—, or —CR$_2$—;
R = hydrogen, lower alkyl or phenyl;
T = methallyl or allyl; and
Me = methyl.

The extended hubs include compounds of the formulae:

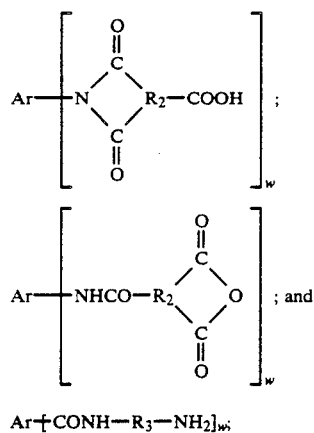

Ar—[CONH—R₃—NH₂]_w;

wherein
- Ar = an aromatic radical of valence w;
- w = 3 or 4; and
- R₃ = a divalent organic radical.

BEST MODE CONTEMPLATED FOR THE INVENTION

Solvent-resistant polyamideimides of the present invention comprise a broad family of linear and multidimensional oligomers having one or two crosslinking functionalities on each end of the molecule. The crosslinking functionalities (Y) include residues selected from the group consisting of:

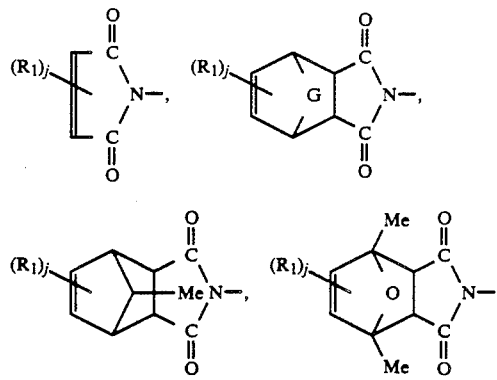

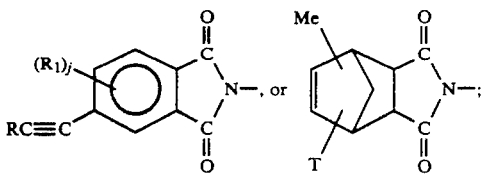

wherein
- $R_1$ = lower alkyl, lower alkoxy, aryl, aryloxy, substituted alkyl, substituted aryl (either including hydroxyl or halo-substituents), halogen, or mixtures thereof;
- j = 0, 1, or 2;
- G = —CH₂—, —O—, —S—, —SO₂—, —SO—, —CO—, —CHR—, or —CR₂—
- R = hydrogen lower alkyl, or phenyl;
- T = methallyl or allyl; and
- Me = methyl.

The amideimides are characterized by backbones of two general types, namely:

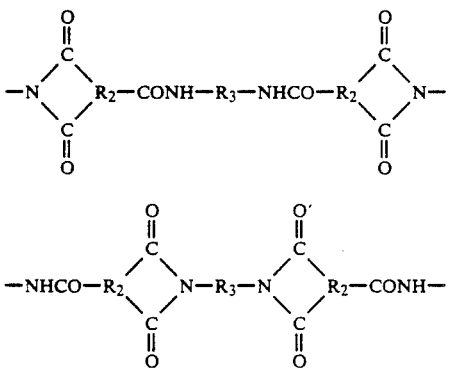

wherein
- $R_3$ = an aromatic, aliphatic, or alicyclic radical, and preferably a phenoxyphenyl sulfone; and
- $R_2$ = a trivalent organic radical, and preferably phenyl.

Accordingly, linear polyamideimides include oligomers of the general formula:

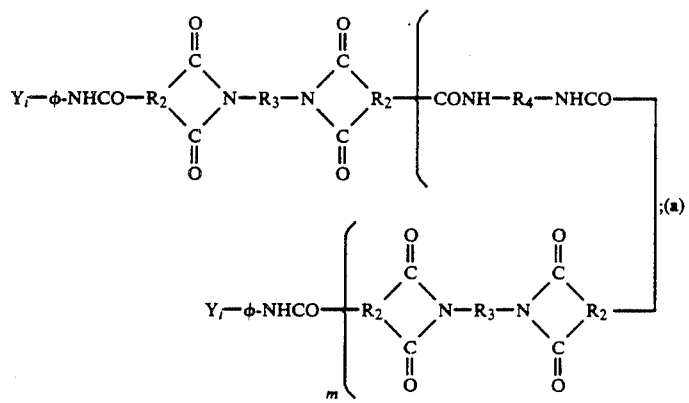

-continued
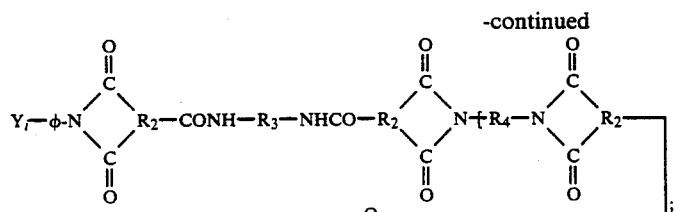
(b)
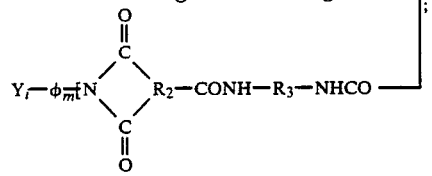
(c)
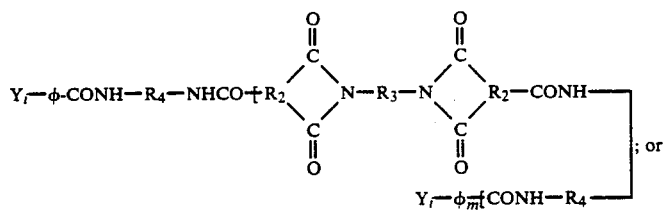
; or
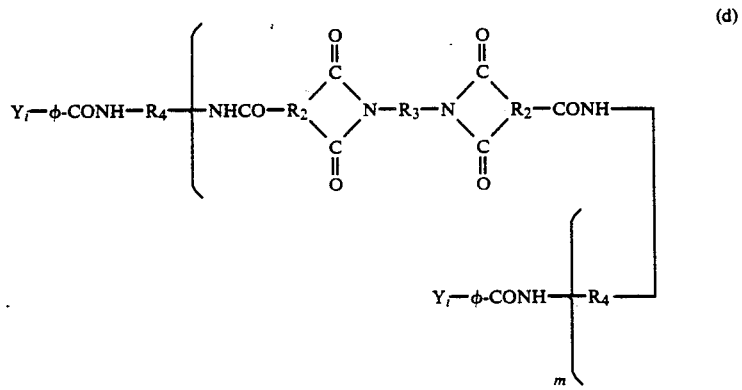
(d)
wherein Y, $R_2$, and $R_3$ are as previously defined, $R_4$=a divalent organic radical, m=a small integer, usually from 0–5, but generally sufficiently large to impart thermoplastic properties on the oligomer, and $\phi$=phenyl.
The multidimensional polyamideimide oligomers include oligomers of the general formula:
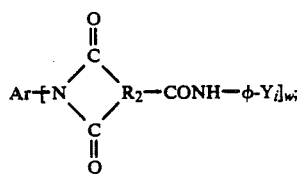
(e)
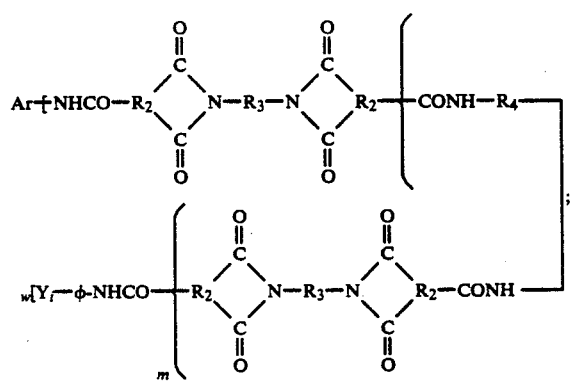
(f)

-continued
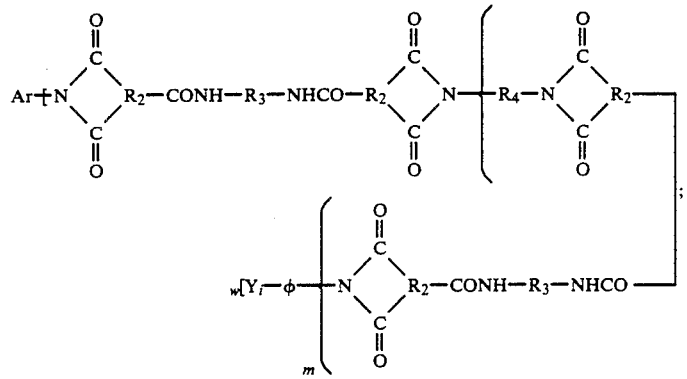 (g)
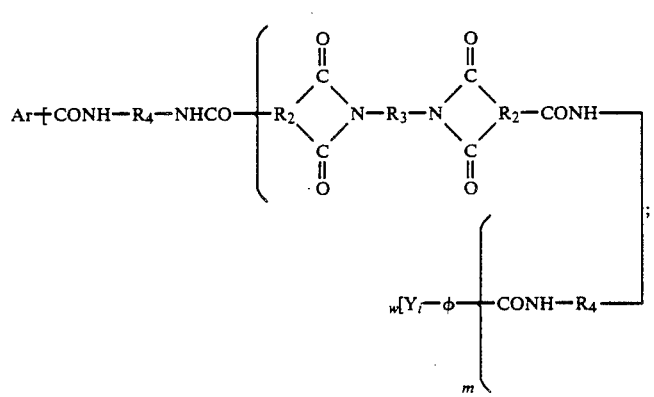 (h)
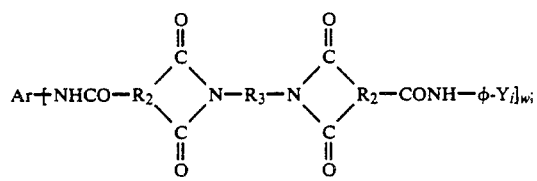 (i)
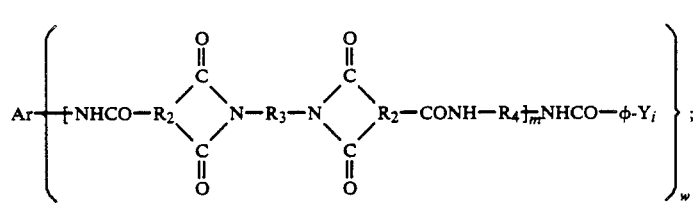 (j)
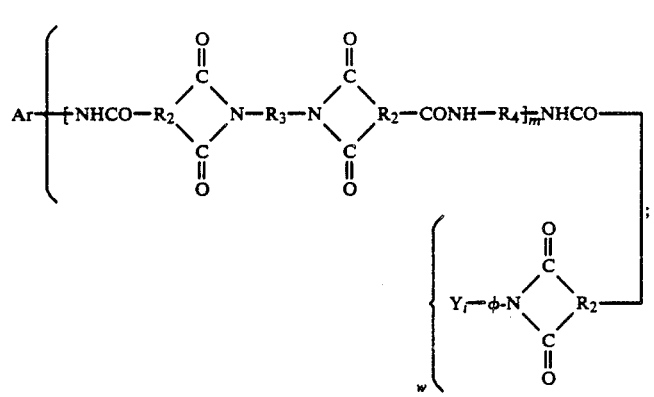 (k)

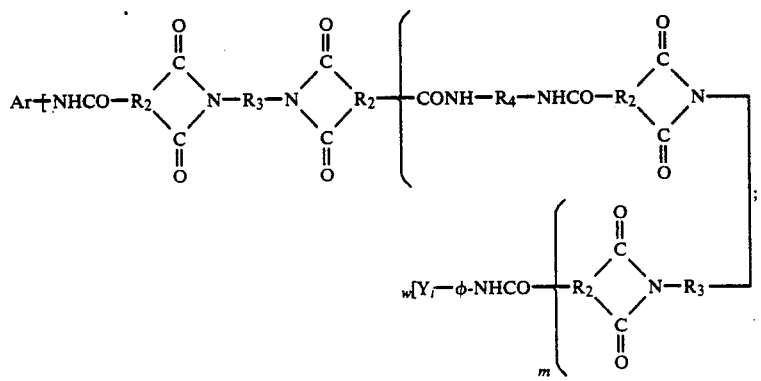
(l)
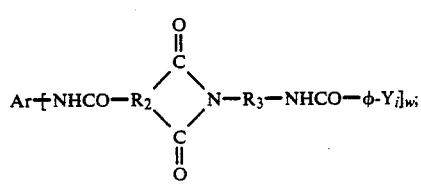
(m)
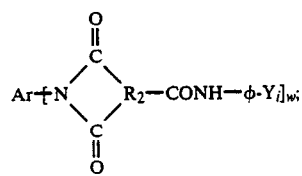
(n)
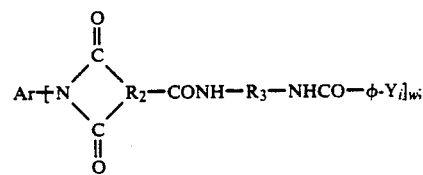
(o)
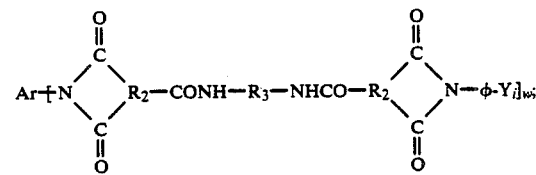
(p)
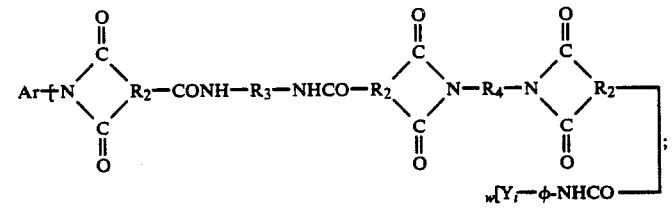
(q)
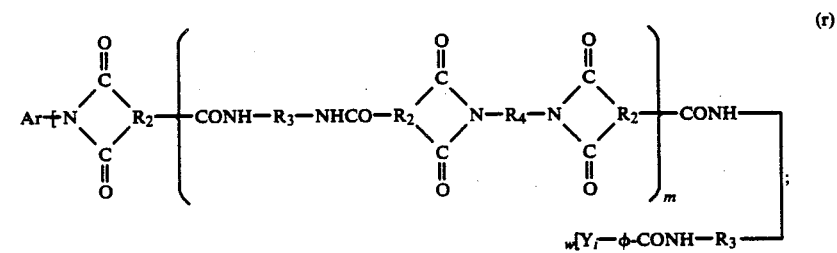
(r)

(s)
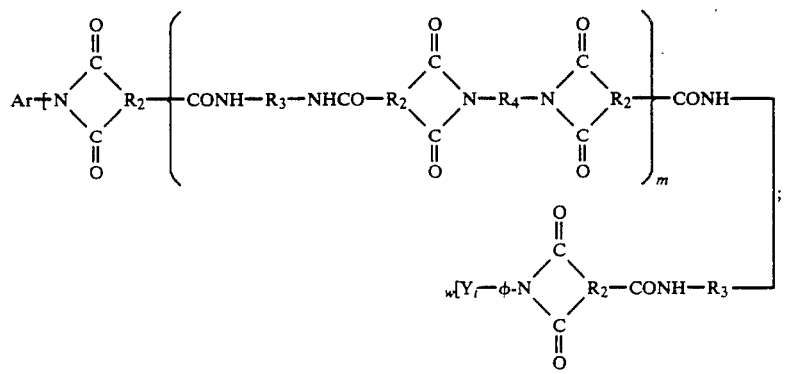

(t)
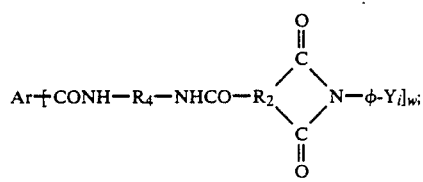

(u)
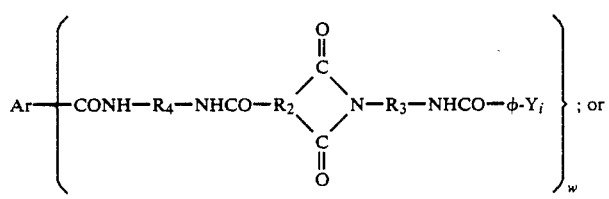

(v)
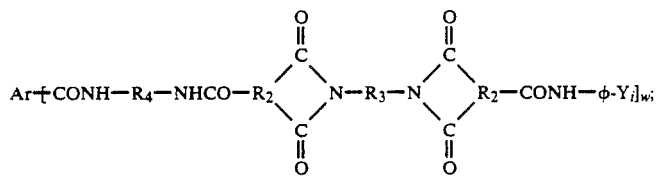

wherein Y, $R_2$, $R_3$, $R_4$, and m are as previously defined, Ar=an organic radical of valency w; $\phi$=phenyl, and w=3 or 4. Preferably, Ar is an aromatic radical (generally phenyl) selected from phenyl, naphthyl, biphenyl, azalinyl (such as melamine), or triazine derivatives of the general formula:

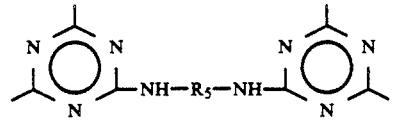

wherein $R_5$=a divalent hydrocarbon residue containing 1-12 carbon atoms, as described in U.S. Pat. No. 4,574,154.

The hub may also be a residue of an etheranhydride of the formula:

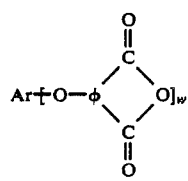

or an etheramine of the formula:

$$Ar-O-\phi-NH_2]_w$$

other hubs will be described when the multidimensional oligomers are discussed in greater detail.

The amideimides are generally made by condensing suitable end cap monomers, diacid halides, diamines, and dianhydrides. The dianhydrides can be prepared by condensing 2 moles of an acid halide anhydride of the formula:

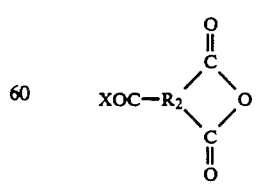

with a diamine of the formula: $H_2N-R_3-NH_2$. The diamine, in this case, can be selected from the group consisting of:

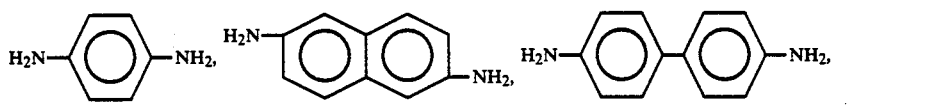
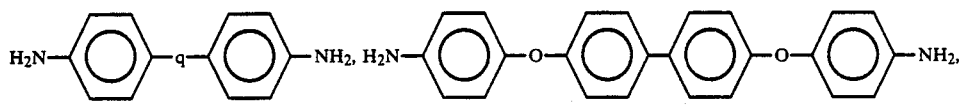
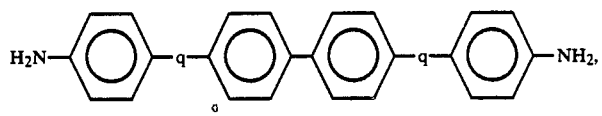
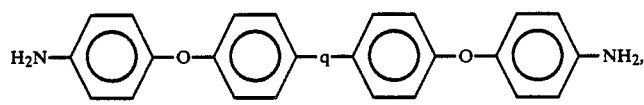
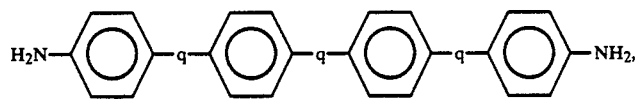
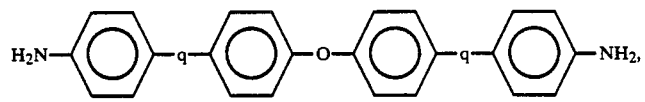
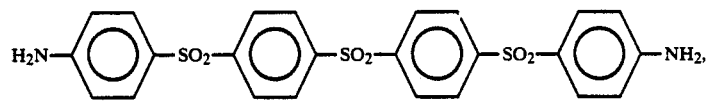
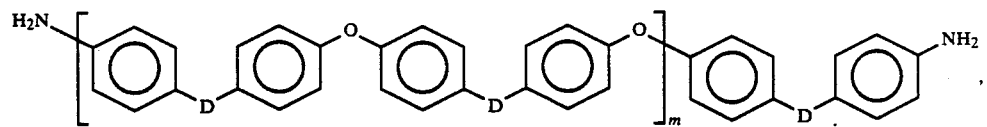
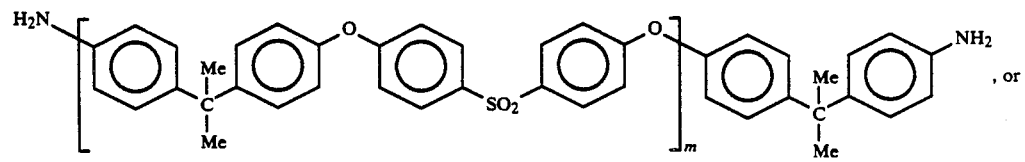
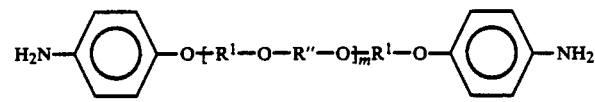
wherein $R^1 =$ 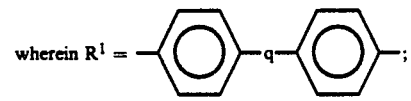;
$R'' =$ 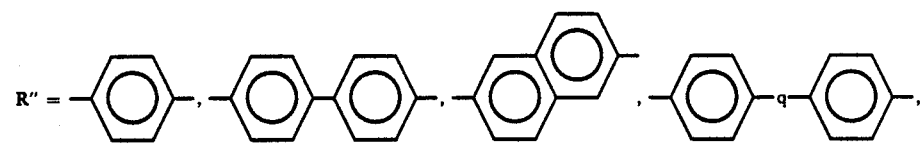

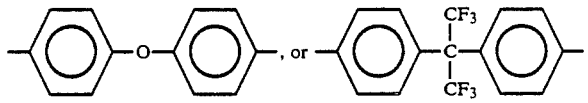

q = —SO₂—, —CO—, —S—, or —(CF₃)₂C—;
Me = methyl;
m = a small integer; and
D = —CO—, —SO₂—, —(CF₃)₂C— or mixtures thereof.

Diamines may include "Schiff base" conductive linkages (particularly —N=CH—), analogous to diacid halides which will be described.

Other diamines that may be used, but that are not preferred, include those described in U.S. Pat. Nos. 4,504,632; 4,058,505; 4,576,857; 4,251,417; and 4,215,418. The aryl or polyaryl "sulfone" diamines previously described are preferred, since these diamines are soluble in conventional synthetic solvents and provide high thermal stability to the resulting oligomers and composites.

Particularly preferred ethersulfone (i.e. phenoxyphenyl sulfone) diamines are those in which $R_1$ is

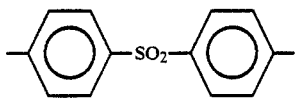

and R'' is

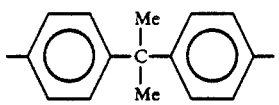

so that the phenoxyphenyl sulfone diamines include:

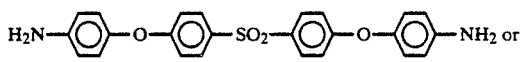

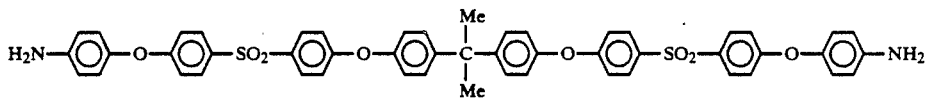

The molecular weights of these diamines can be easily varied from approximately 500 to about 2000. Using lower molecular weight diamines enhances the mechanical properties of the difunctional polyamideimide oligomers, each of which has alternating ether "sulfone" segments in the backbone.

Phenoxyphenyl sulfone diamines of this qeneral nature can be prepared by reacting two moles of aminophenol with (n+1) moles of an aryl radical having terminal, reactive halide functional groups (dihalogens), such as 4,4'-dichlorodiphenyl sulfone, and a suitable bisphenol (i.e., dihydric phenol or diol). The bisphenol is preferably selected from the group consisting of:
2,2-bis-(4-hydroxyphenyl)-propane (i.e., bisphenol-A);
bis-(2-hydroxyphenyl) methane;
bis-(4-hydroxyphenyl)-methane;
1,1-bis-(4-hydroxyphenyl)-ethane;
1,2-bis-(4-hydroxyphenyl)-ethane;
1,1-bis-(3-chloro-4-hydroxyphenyl)-ethane;
1,1-bis-(3,5-dimethyl-4-hydroxyphenyl)-ethane;
2,2-bis-(3-phenyl-4-hydroxyphenyl)-propane;
2,2-bis-(4-hydroxynaphthyl)-propane
2,2-bis-(4-hydroxyphenyl)-pentane;
2,2-bis-(4-hydroxyphenyl)-hexane;
bis-(4-hydroxyphenyl)-phenylmethane;
bis-(4-hydroxyphenyl)-cyclohexylmethane;
1,2-bis-(4-hydroxyphenyl)-1,2-bis-(phenyl)-ethane;
2,2-bis-(4-hydroxyphenyl)-1-phenylpropane;
bis-(3-nitro-4-hydrophenyl)-methane;
bis-(4-hydroxy-2,6-dimethyl-3-methoxyphenyl)-methane;
2,2-bis-(3,5-dichloro-4-hydroxyphenyl)-propane;
2,2-bis-(3-bromo-4-hydroxyphenyl)-propane;
or mixtures thereof, as disclosed in U.S. Pat. No. 3,262,914. Bisphenols having aromatic character (i.e., absence of aliphatic segments), such as bisphenol-A, are preferred.

The dihalogens in this circumstance preferably are selected from the group consisting of:

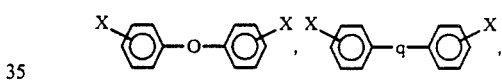

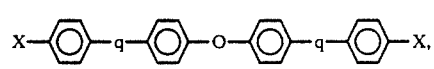

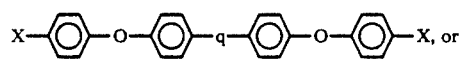

wherein
X = halogen, preferably chlorine; and
q = —S—, —SO₂—, —CO—, —(CH₃)₂C—, and —(CF₃)₂C—, and preferably either —SO₂— or —CO—.

The condensation reaction creates ether diamines that ordinarily include intermediate "sulfone" linkages. The condensation generally occurs through a phenate mechanism in the presence of K₂CO₃ or another base in a DMSO/toluene solvent.

The grain size of the K₂CO₃(s) should fall within the 100–250 ANSI mesh range.

Additional methods for preparing phenoxyphenysulfones of this general type are disclosed in U.S. Pat. Nos. 3,839,287 and 3,988,374.

The diacid halide or dicarboxylic acid may include an aromatic chain segment selected from the group consisting of:

phenyl; naphthyl; biphenyl;

a polyaryl "sulfone" divalent radical of the general formula:

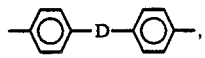

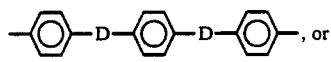, or

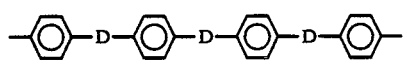

wherein
D=—S—, —O—, —CO—, —SO$_2$—, —(CH$_3$)$_2$C—, —(CF$_3$)$_2$C—,
or mixtures thereof throughout the chain; or a divalent radical having conductive linkages, illustrated by Schiff base compounds selected from the group consisting of:

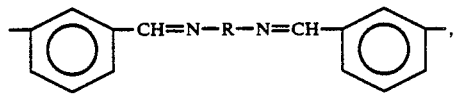

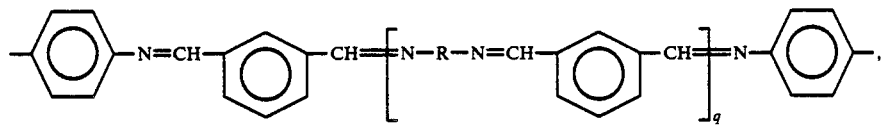

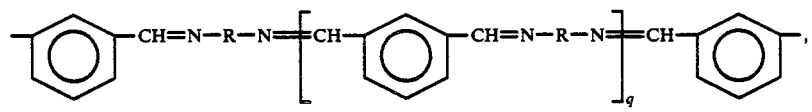

wherein
R is selected from the group consisting of: phenyl; biphenyl; naphthyl; or a divalent radical of the general formula:

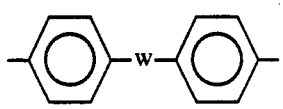

wherein
W=—SO$_2$— or —CH$_2$—; and q=0-4; or a divalent radical of the general formula:

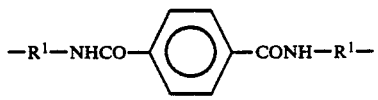

wherein
R$^1$=a C$_2$ to C$_{12}$ divalent aliphatic, alicyclic, or aromatic radical, and, preferably, phenyl (as described in U.S. Pat. No. 4,556,697).

Thiazole, oxazole, or imidazole linkages, especially between aryl groups, may also be used in the conductive or semiconductive oligomers.

The preferred diacid halides include:

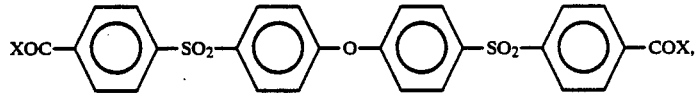

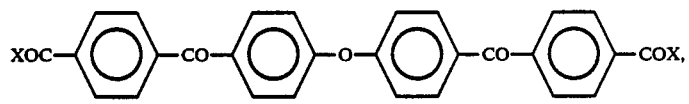

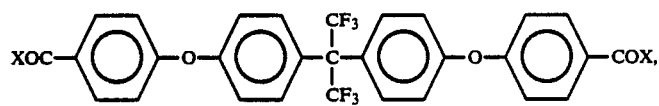

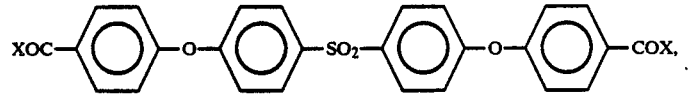

-continued

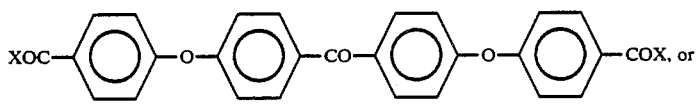

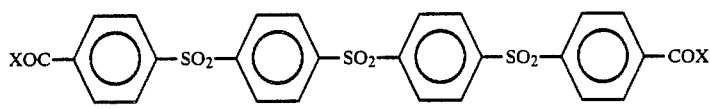

Schiff base dicarboxylic acids and diacid halides can be prepared by the condensation of aldehydes and aminobenzoic acid (or other amine acids) in the general reaction scheme:

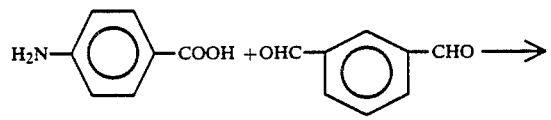

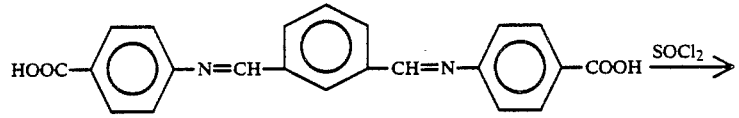

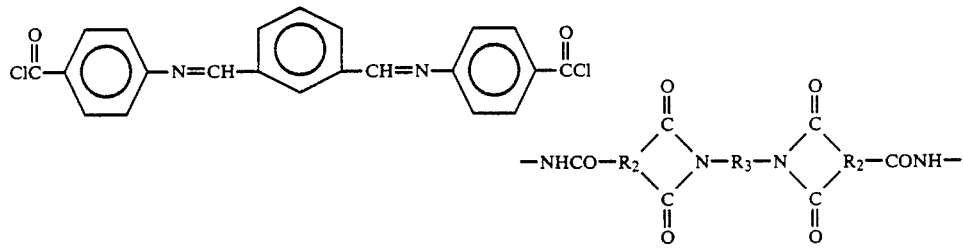

or similar schemes.

Other diacid halides that can be used, but that are not preferred, are disclosed in U.S. Pat. No. 4,504,632, and include:
adipylchloride,
malonyl chloride,
succinyl chloride,
glutaryl chloride,
pimelic acid dichloride,
suberic acid dichloride,
azelaic acid dichloride,
sebacic acid dichloride,
dodecandioic acid dichloride,
phthaloyl chloride,
isophthaloyl chloride,
terephthaloyl chloride,
1,4-naphthalene dicarboxylic acid dichloride, and
4,4'-diphenylether dicarboxylic acid dichloride.

Polyaryl or aryl diacid halides are preferred to achieve the highest thermal stabilities in the resulting oligomers and composites insofar as aliphatic bonds are not as thermally stable as aromatic bonds. Particularly preferred compounds include intermediate "sulfone" linkages to improve toughness of the resulting oligomers. For purposes of this description, "sulfone" linkages include —SO$_2$—, —S—, —CO—, and —(CF$_3$)$_2$C—, unless clearly limited to only —SO$_2$—.

The corresponding amideimide of the formula:

can be prepared if the acid anhydride:

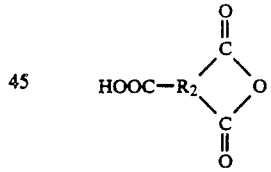

is used instead of the acid halide anhydride. The resulting intermediate products are dicarboxylic acids rather than dianhydrides. These dicarboxylic acids (or their diacid halides) can be used with the diamines previously described.

Dianhydrides for the amideimide synthesis include:
(a) pyromellitic dianhydride,
(b) benzophenonetetracarboxylic dianhydride (BTDA), and
(c) 5-(2,5-diketotetrahydrofuryl)-3-methylcyclohexene-1,2-dicarboxylic anhydride (MCTC), but may be any aromatic or aliphatic dianhydride, such as those disclosed in U.S. Pat. Nos. 3,933,862; 4,504,632; 4,577,034; 4,197,397; 4,251,417; 4,251,418; or 4,251,420. Mixtures of dianhydrides might be used. Lower molecular weight dianhydrides are preferred, and MCTC or other aliphatic dianhydrides are the most preferred for the lower curing polyamideimides having caps with two crosslinking functionalities.

Of course, the dianhydrides also include those intermediates resulting from the condensation of the acid halide anhydride with any of the diamines previously described. Similarly, the dicarboxylic acids and diacid halides include those intermediates prepared by the condensation of the acid anhydride with any of the diamines previously described. The corresponding dicarboxylic acid is converted to the diacid halide (i.e. chloride) in the presence of $SOCl_2$.

Conductive oligomers of the present invention include conductive linkages like a "Schiff base" and generally exhibit greater oxidative stability and greater dimensional stability at elevated temperatures, greater impact strengths, greater dimensional stiffness over a wider range of temperatures, and greater toughness than prior art conductive oligomers and composites.

Dopants for creating semiconductive or conductive composites with "Schiff base" oligomers are preferably selected from compounds commonly used to dope other polymers, namely, (1) dispersions of alkali metals (for high activity) or (2) strong chemical oxidizers, particularly alkali perchlorates (for lower activity). Arsenic compounds and elemental halogens, while active dopants, are too dangerous for general usage, and are not recommended.

The dopants react with the oligomers or polymers to form charge transfer complexes. N-type semiconductors result from doping with alkali metal dispersions. P-type semiconductors result from doping with elemental iodine or perchlorates. Dopant should be added to the oligomer or blend prior to forming the prepreg.

While research into conductive or semiconductive polymers has been active, the resulting compounds (mainly polyacetylenes, polyphenylenes, and polyvinylacetylenes) are unsatisfactory for aerospace applications because the polymers are:

(a) unstable in air;
(b) unstable at high temperatures;
(c) brittle after doping;
(d) toxic because of the dopants; or
(e) intractable.

These problems are overcome or significantly reduced with the conductive oligomers of the present invention.

As used in describing the suitable diacid halides and diamines, "Schiff base" is used throughout this specification in a generic way rather than in its typical chemical way, and is used to represent as well other conductive linkages, such as oxazoles, thiazoles, or imidazoles.

While conventional theory holds that semiconductive polymers should have (1) low ionization potentials, (2) long conjugation lengths, and (3) planar backbones, there is an inherent trade-off between conductivity and toughness or processibility, if these constraints are followed. To overcome the processing and toughness shortcomings common with Schiff base, oxazole, imidazole, or thiazole polymers, the oligomers of the present invention, include "sulfone" linkages interspersed along the backbone providing a mechanical swivel for the rigid, conductive segments of the arms. Phenoxyphenylsulfone or phenoxyphenylketone moieties are preferred. The resulting compounds are polyphenoxyphenylsulfoneimido oligomers with conductive segments.

Thermally stable, conductive or semiconductive oligomers having the multidimensional morphology may also be synthesized, and generally are synthesized to include a high degree of aromatic groups. The stable aromatic bond energies allow synthesis of an oligomer having outstanding thermal stability. Acceptable toughness and impact resistance is gained (as with the linear oligomers) through electronegative linkages within the linear chains of aromatic groups that radiate from the central aromatic hub. The electronegative linkages ("sulfone" linkages) include the groups: —CO—; —SO$_2$—; —(CF$_3$)$_2$C—; and —S—. Generally, —CO— and —SO$_2$— groups are preferred for cost, convenience, and performance. The group —S—S— should be avoided, since it is too thermally labile.

The preferred aromatic moieties are aryl groups, such as phenyl, biphenyl, and naphthyl. Other aromatic groups can be used, if desired, since their stabilized aromatic bonds should provide the desired thermal stability. For example, azaline groups may be used. As discussed earlier, the aryl groups may include substituents, if desired, such as halogen, lower alkyl up to about 4 carbon atoms, lower alkoxy up to about 4 carbon atoms, or aryl side chains. Steric hindrance may arise in synthesizing the oligomers or in crosslinking the oligomers into cured composites, if the side chains are too large. The substituents may also effect the thermal stability of the resulting oligomers and composites. Unsubstituted phenyl groups are preferred for cost, convenience, and performance. The m-isomer may be preferred, since it tends to create a folded ribbon structure in the backbone.

In the multidimensional oligomers, an aromatic hub includes a plurality of rays or spokes radiating from the hub in the nature of a star to provide multidimensional crosslinking through suitable terminal groups with a greater number (i.e. higher density) of crosslinking bonds than linear arrays provide. Usually the hub will have three radiating chains to form a "Y" pattern. In some cases, four chains may be used. Including more chains leads to steric hindrance as the hub is too small to accommodate the radiating chains. A trisubstituted phenyl hub is highly preferred with the chains being symmetrically placed about the hub. Biphenyl, naphthyl, or azaline (e.g., melamine) may also be used as the hub radical along with other aromatic moieties, if desired.

The best results are likely to occur when the arm length is as short as possible and the oligomer has six crosslinking sites. The most preferred hub includes the phenyl radical, since these compounds are relatively inexpensive, are more readily obtained, and provide oligomers with high thermal stability.

The chains of the oligomers include crosslinking end groups which improve the solvent-resistance of the cured composites. These end groups may be thermally or chemically activated during the curing step to provide a strongly crosslinked, complex, multidimensional array of interconnected oligomers. When the goal is an advanced composite having a glass transition temperature above 900° F. (and preferably above 950° F.) each end cap should have high thermal stability and a high thermal activation temperature. End caps with two crosslinking functionalities (difunctional end caps) are expected to yield the highest crosslinked arrays.

Triazine derivatives can be used as the hub. These derivatives are described in U.S. Pat. No. 4,574,154 and have the general formula:

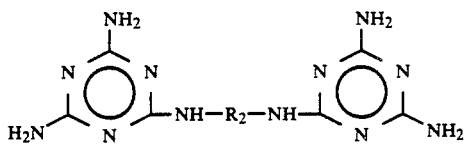

wherein $R_2$ is a divalent hydrocarbon residue containing 1-12 carbon atoms (and, preferably, ethylene). The polybasic triazine derivatives of U.S. Pat. No. 4,617,390 (or the acid halides) can also be used as the hub.

Yet another class of hubs (aryletheramines) can be formed by reacting the corresponding halo-hub (such as tribromobenzene) with aminophenol to form triamine compounds represented by the formula:

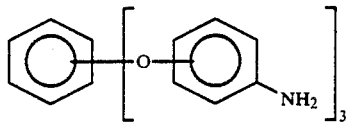

The oligomers may be formed by the attachment of arms to the hub followed by chain extension and chain termination. For example, trihydroxybenzene may be mixed with p-aminophenol and 4,4'-dibromodiphenylsulfone and reacted under an inert atmosphere at an elevated temperature to achieve an amino terminated "star" of the general formula:

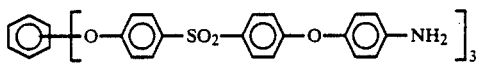

that can be reacted with suitable diacid halides, diamines, and end caps to yield a polyamideimide oligomer.

The hub may also be a residue of an etheranhydride of the formula:

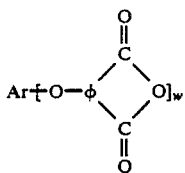

which can be synthesized by reacting nitro- or halophthalic anhydride with Ar—(OH)$_w$ in a suitable solvent under an inert atmosphere, as described generally in our copending application, U.S. Ser.No. 07/016,703 filed Feb. 20, 1987, U.S. Pat. No. 4,851,495 and in U.S. Pat. No. 3,933,862 (thio-analogs).

The compounds might be made by reacting nitrophthalic anhydride with an amine end cap followed by the condensation with a polyol (hydroxy) hub or in similar reaction schemes that will be understood by those of ordinary skill.

Carboxylic acid hubs include cyuranic acid, those compounds described in U.S. Pat. No. 4,617,390, and compounds prepared by reacting polyols, such as phloroglucinol, with nitrobenzoic acid or nitrophthalic acid to form ether linkages and active, terminal carboxylic acid functionalities. The nitrobenzoic acid products would have three active sites while the nitrophthalic acid products would have six; each having the respective formula:

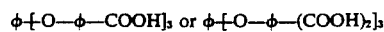

wherein $\phi$=phenyl. Of course other nitro-acids can be used.

Hubs can also be formed by reacting the corresponding halo-hub (such a tribromobenzene) with aminophenol to form triamine compounds represented by the formula:

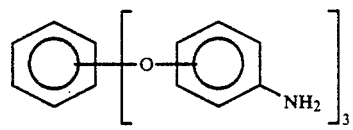

which can then be reacted with an acid anhydride to form a polycarboxylic acid of the formula:

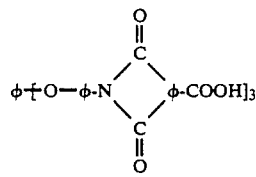

wherein 0=phenyl; the hub being characterized by an intermediate ether and imide linkage connecting aromatic groups. Thio-analogs are also contemplated, in accordance with U.S. Pat. No. 3,933,862.

The hub may also be a polyol such as those described in U.S. Pat. No. 4,709,008 to tris(hydroxyphenyl)alkanes of the general formula:

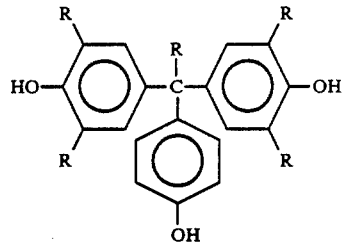

wherein R=hydrogen or methyl and can be the same or different. The polyols are made by reacting, for example, 4-hydroxy-benzaldehyde or 4-hydroxyacetophenone with an excess of phenol under acid conditions (as disclosed in U.S. Pat. Nos. 4,709,008; 3,579,542; and 4,394,469). The polyols are generally reacted with nitrophthalic anhydride, nitroaniline, or nitrobenzoic acids to form the actual reactants that are suitable as hubs, as will be understood by those of ordinary skill.

Phenoxyphenyl sulfone arms radiating from a hub with a terminal amine, carboxylic acid, or anhydride group are also precursors for making multidimensional oligomers of the present invention.

The oligomers can be synthesized in a homogeneous reaction scheme wherein all the reactants are mixed at one time, or in a stepwise reaction scheme wherein the radiating chains are affixed to the hub and the product of the first reaction is subsequently reacted with the end cap groups. Of course, the hub may be reacted with end-capped arms that include one reactive, terminal functionality for linking the arm to the hub. Homogeneous reaction is preferred, resulting undoubtedly in a mixture of oligomers because of the complexity of the reactions. The products of the processes (even without distillation or isolation of individual species) are preferred oligomer mixtures which can be used without further separation to form the desired advanced composites.

Linear or multidimensional oligomers can be synthesized from a mixture of four or more reactants so that extended chains may be formed. Adding components, however, adds to the complexity of the reaction and of its control. Undesirable competitive reactions may result or complex mixtures of macromolecules having widely different properties may be formed, because the chain extenders and chain terminators are mixed, and compete with one another.

Because the oligomers (resins) synthesized in accordance with this invention generally have appreciable molecular weight between the reactive (crosslinking) groups, the oligomers will retain sufficient plasticity to be processible during fabrication prior to crosslinking of the end caps to thermoset composites. If possible, thermoplastic formulations with even higher molecular weights should be synthesized. The resins preferably have MWs (average formula weights) between about 5,000–40,000, and, more preferably, between about 15,000–25,000.

Solubility of the oligomers becomes an increasing problem as chain length increases. Therefore, shorter chains are preferred, if the resulting oligomers remain processible. That is, the chains should be long enough to yield thermoplastic characteristics to the oligomers but short enough to keep the oligomers soluble during the reaction sequence.

Blends can improve impact resistance of composites prepared from the crosslinkable oligomers without causing a significant loss of solvent resistance. The blends comprise mixtures of one or more crosslinkable oligomers and one or more polymers that are incapable of crosslinking, and generally comprise substantially equimolar amounts of one polymer and an oligomer having substantially identical backbones. The crosslinkable oligomer and comparable polymer can be blended together by mixing mutually soluble solutions of each. While the blend is preferably equimolar in the oligomer and polymer, the ratio of the oligomer and polymer can be adjusted to achieve the desired physical properties.

Although the polymer in the blend usually has the same length backbone (and comparable average formula weight) as the oligomer, the properties of the composite formed from the blend can be adjusted by altering the ratio of formula weights for the polymer and oligomer. The oligomer and polymer generally have substantially identical repeating units, but the oligomer and polymer merely be compatible in the solution prior to sweeping out as a prepreg. Of course, if the polymer and oligomer have identical backbones, compatibility in the blend is likely to occur.

Quenching compounds can be employed, if desired to regulate the polymerization of the comparable polymer, so that it has an average formula weight substantially identical with the crosslinkable oligomer. For thermal stability, an aromatic quenching compound, such as aniline, is preferred.

Solvent resistance may decrease markedly if the comparable polymer is provided in large excess to the crosslinkable oligomer in the blend.

The blends will generally comprise a mixture of an amideimide oligomer and an amideimide polymer. The polymer may, however, be from another family, such as an imide or an amide. The mixture may include multiple oligomers or multiple polmers, such as a three component mixture of an amideimide oligomer, an amide oligomer, and an imide polymer. Etherimide oligomers or polymers may be suitable in such blends. A blend might include amideimides and etherimides with either or both resin including crosslinking end caps. We described a family of etherimides in our copending U.S. patent application 07/016,703 filed Feb. 20, 1987, U.S. Pat. No. 4,851,495. Of course, any compatible polymer may be blended with the amideimide oligomers.

The blends may yield semi-interpenetrating networks of the general type described by Egli et al. "Semi-Interpenetrating Networks of LARC-TPI" available from NASA- Langley Research Center.

The amideimides of the present invention can be synthesized by several schemes, as previously described. To obtain repeating units of the general formula:

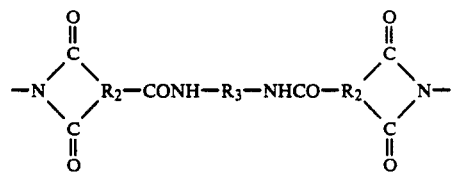

an acid halide anhydride particularly

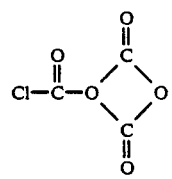

can be mixed with a diamine and with an amine end cap in the ratio of n:n:2 wherein n=an integer greater than or equal to 1. In this reaction, the acid halide anhydride will react with the diamine to form an intermediate dianhydride which will condense with the diamine and amine end cap. The reaction may be carried out in two distinct stages under which the dianhydride is first prepared by mixing substantially equimolar amounts (or excess diamine) of the acid halide anhydride and diamine followed by the addition of a mixture of the diamine and the end cap. Of course, the diamine used to form the dianhydride may differ from that used in the second stage of the reaction, or it may be a mixture of diamines from the outset.

The related amideimide having repeating units of the general formula:

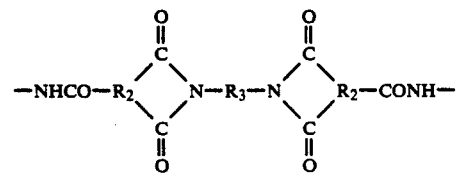

can be synthesized by reacting the acid anhydride with the diamine to form intermediate dicarboxylic acids, which can then react with more diamine, another diamine, or an amine end cap to complete the oligomer. Again, the reaction can be divided into steps.

The oligomers appear to possess greater solvent resistance if the condensation of the dianhydride/dicarboxylic acid with the diamine and end cap is done simultaneously rather than sequentially.

While use of an amine end cap has been described above, corresponding oligomers can be formed by using an acid halide end cap, if the diamine is provided in excess. In this case the reaction mixture generally comprises the acid halide anhydride or the acid anhydride, the end cap, and the diamine and the synthesis is completed in one step.

All reactions should be conducted under an inert atmosphere and at elevated temperatures, if the reaction rate needs to be increased. The reaction mixture should be well stirred throughout the synthesis. Chilling the reaction mixture can slow the reaction rate and can assist in controlling the oligomeric product.

As suggested in U.S. Pat. No. 4,599,383, the diamine may be in the form of its derivative OCN—R—NCO, if desired.

The invention relates broadly to capped amideimide resins. The amideimides described in U.S. Pat. Nos. 4,599,383; 3,988,374; 4,628,079; 3,658,938; and 4,574,144 can all be capped with the crosslinking monomers to convert the polymers to oligomers of the present invention that are suitable for advanced composites.

Suitable end cap monomers include unsaturated hydrocarbons of the general formula:

$$Y_i-R-Q$$

wherein
i = 1 or 2;
Q = —NH$_2$ or —COX;
X = halogen, preferably chlorine;
R = a phenyl or pyrimidine radical;
Y =

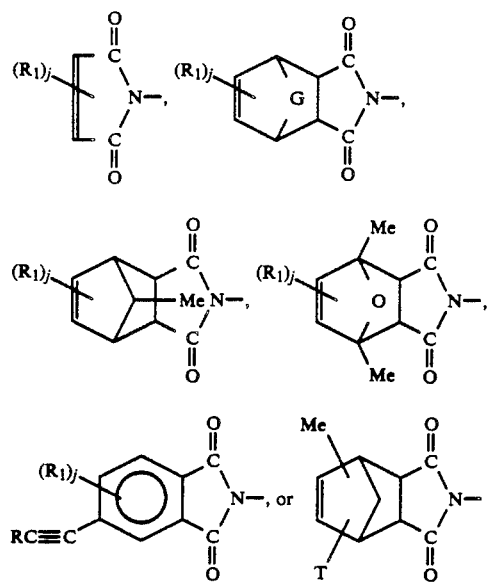

$R_1$ = lower alkyl, lower alkoxy, aryl, aryloxy, substituted alkyl, substituted aryl (either including hydroxyl or halo-substituents), halogen, or mixtures thereof;
j = 0, 1, or 2;
G = —CH$_2$—, —O—, —S—, —SO$_2$—, —SO—, —CO—, —CHR—, or —CR$_2$—
R = hydrogen, lower alkyl, or phenyl;
T = methallyl or allyl; and
Me = methyl.

The end cap monomers are prepared by condensing the respective anhydrides with (H$_2$N$\rightarrow$)$_2$—R—Q, in the manner described in U.S. Pat. No. 4,604,437 with respect to the allyl- or methallyl-substituted methylbicyclo[2.2.1]hept-5-ene-2,3-dicarboximides. A phenyl counterpart of the halopyrimidine cap can be made using a halo-substituted diaminobenzene.

The aromatic character of the pyrimidine ring should provide substantially the same benefits as the phenyl ring. The thermo-oxidative stability of the resulting composites, however, might be somewhat less than that achieved for the phenyl end cap monomers.

Generally the amine end cap monomer will be prepared for synthesizing the corresponding acid halide and converting the —COX functionality to an amine through the acid amide in the presence of ammonia, as described in U.S. Ser. No. 07/046,202 filed May 4, 1987, U.S. Pat. No. 4,935,523.

The pyrimidine precursors are described in U.S. Pat. No. 3,461,461.

The oligomers and blends of the present invention can be combined with reinforcing materials and cured to composite materials using heat or chemicals to activate crosslinking or interlinking between end caps. Prepregs can be prepared by conventional prepregging techniques. While woven fabrics are the typical reinforcement, the fibers can be continuous or discontinuous (in chopped or whisker form) and may be ceramic, organic, carbon (graphite), or glass, as suited for the desired application. Curing generally is conducted in conventional vacuum bagging techniques at elevated temperatures. The curing temperature varies with the choice of end cap. If desired, mixtures of end caps might be used.

The oligomers and blends of the present invention can also be used as adhesives, varnishes, films, and coatings.

Although polyaryl compounds are generally described, aliphatic moieties can be included in the backbones, in some cases, although the ultimate use temperatures of these oligomers or composites may be lower than those oligomers that have entirely polyaryl backbones.

While para isomerization is generally shown, other isomers are possible. Furthermore, the aryl groups can have substituents, if desired, such as halogen, lower alkyl up to about 4 carbon atoms, lower alkoxy up to about 4 carbon atoms, or aryl. Substituents may create steric hindrance problems in synthesizing the oligomers or in crosslinking the oligomers into the final composites.

HYPOTHETICAL EXAMPLES

1. Synthesis of Compound (a)

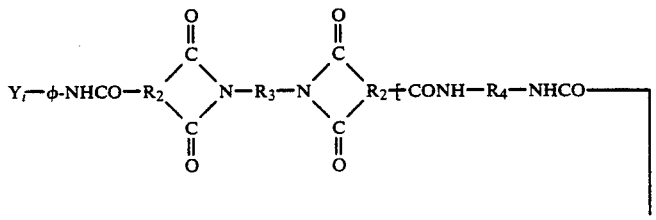

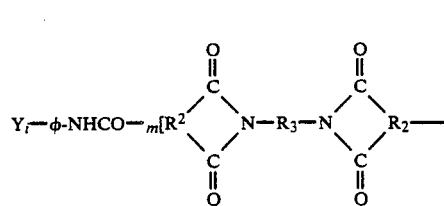

A diamine of the formula $H_2N$—$R_3$—$NH_3$ is reacted with two moles of an acid anhydride of the formula:

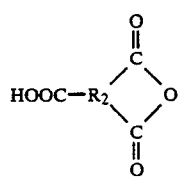

to form a dicarboxylic acid intermediate of the formula:

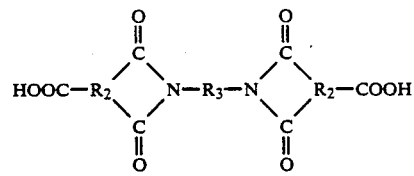

The intermediate is converted to the corresponding diacid chloride in the presence of $SOCl_2$, which is then condensed with one mole of a diamine of the formula $H_2N$—$R_4$—$NH_2$ and two moles of an amine end cap of the formula $Y_i$—$\phi$—$NH_2$ to yield the desired product.

If excess diamine of the formula $H_2N$—$R_4$—$NH_2$ is used along with an acid halide end cap of the formula $Y_i$—$\phi$—COX, the product can have the formula:

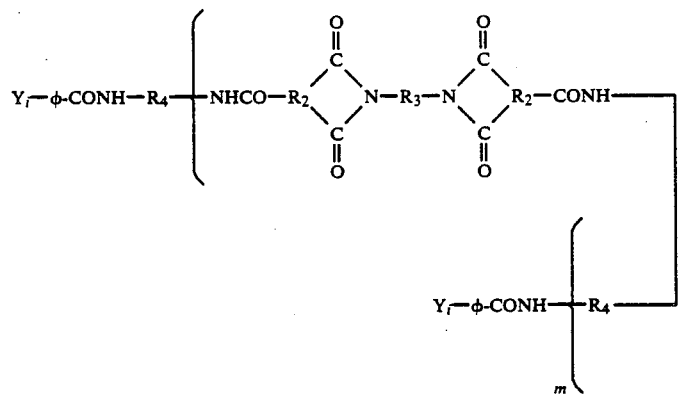

2. Synthesis of Compound (b)

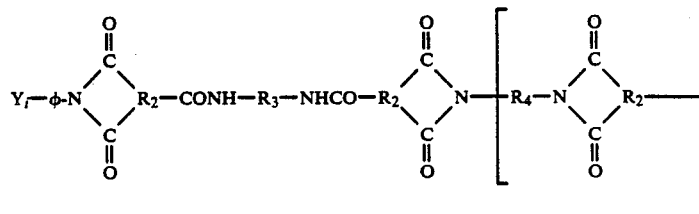

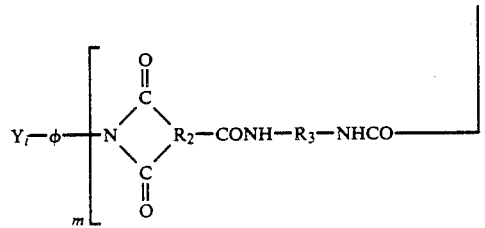

A diamine of the formula $H_2N—R_3—NH_2$ is reacted with

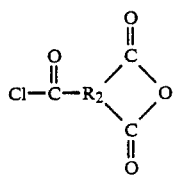

to yield a dianhydride intermediate of the formula:

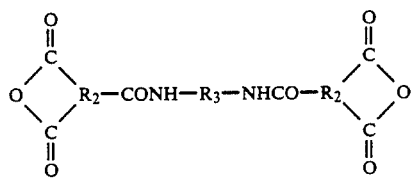

The intermediate is then condensed with $Y_i—\phi—NH_2$ and a diamine of the formula $H_2N—R_4—NH_2$ to yield the desired product.

3. Synthesis of Compound (d)

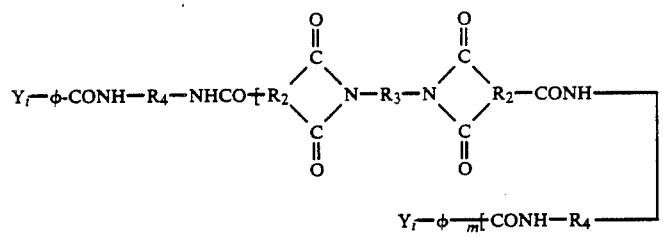

A diamine of the formula $H_2N—R_3—NH_2$ is reacted with an acid anhydride as in Example 1 to form a dicarboxylic acid intermediate that can be reacted with another diamine of the formula $H_2N—R_4—NH_2$ and an acid halide end cap of the formula $Y_i—\phi—COCl$ to yield the desired product.

4. Synthesis of Compound (e)

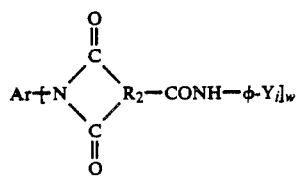

An aromatic hub like triaminobenzene is condensed with a phthalyl acid anhydride and an amine end cap to yield the desired product.

5. Synthesis of Compound (f)

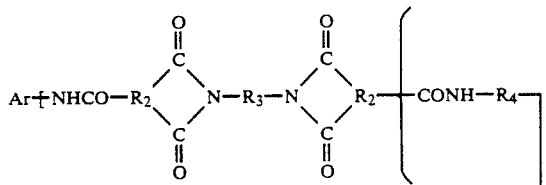

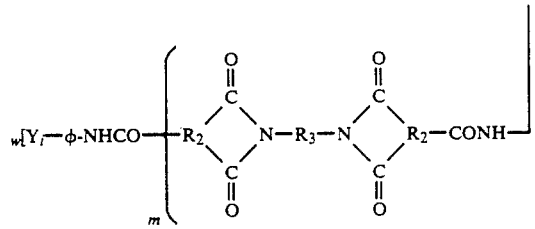

An amine-substituted hub like triaminobenzene, is reacted with the dicarboxylic acid intermediate of Example 1, a diamine of the formula $H_2N—R_4—NH_2$, and an amine end cap in the ratio of 1 mole of hub: (w)(m+1) moles of intermediate:(w)(m) moles of diamine:w moles of end cap to prepare the desired multidimensional product.

6. Synthesis of Compound (g)

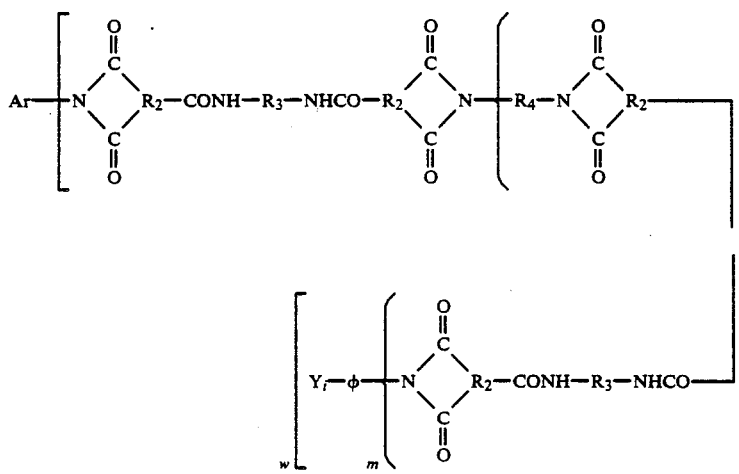

An aromatic amine hub is reacted with the dianhydride intermediate of Example 2, a diamine of the formula H$_2$N—R$_4$—NH$_2$, and an amine end cap on the ratio of 1 mole hub : (w)(m+1) moles dianhydride: (w)(m) moles diamine : w moles end cap to yield the desired product.

7. Synthesis of Compound (h)

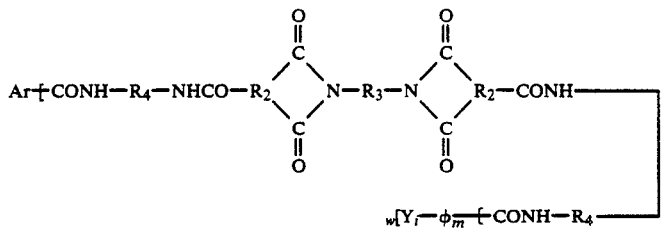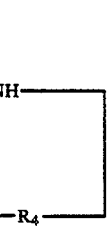

An aromatic acid or acid halide hub, like cyuranic acid, is reacted with a diamine of the formula H$_2$N—R$_4$—NH$_2$, a dicarboxylic acid intermediate of Example 1, and an acid halide end cap in the ratio of 1 mole hub:(w)(m+1) moles diamine:(w)(m) moles intermediate:w moles end cap to yield the desired product.

8. Synthesis of Compound (i)

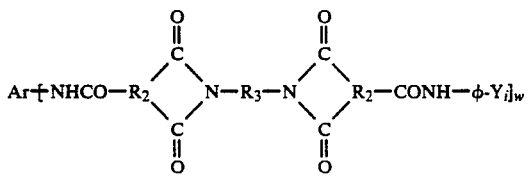

An aromatic amine hub is reacted with a dicarboxylic acid intermediate (or dihalide) of Example 1 and an amine end cap on the ratio of 1 mole hub:w moles intermediate:w moles cap to yield the desired product.

9 Synthesis of Compound (j)

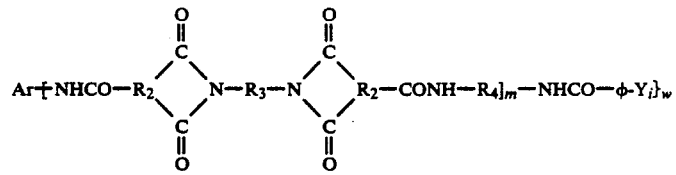

An aromatic amine hub is reacted with the intermediate of Example 8, a diamine, and an acid halide end cap in the ratio of 1 mole hub:w moles intermediate:w moles diamine, and w moles cap to form the desired product.

10. Synthesis of Compound (k)

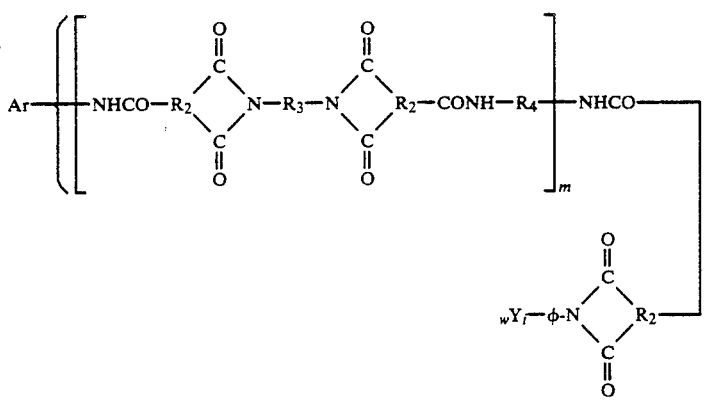

An aromatic amine hub is reacted with the intermediate of Example 1, a diamine of the formula $H_2N-R_4-NH_2$, and an acid or acid halide end cap of the formula:

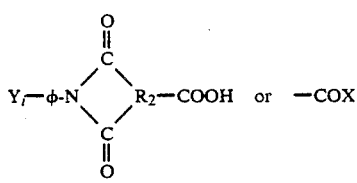

in the ratio of 1 mole hub: (w)(m) moles intermediate:(w)(m) moles diamine : w moles end cap to form the desired product.

The end cap is prepared by condensing an amine end cap of the formula: $Y_i-\phi-NH_2$ with an acid anhydride of the formula:

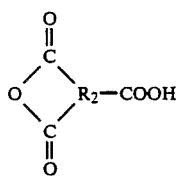

The acid halide is prepared from the acid in the presence of $SOCl_2$.

11. Synthesis of Compound (l)

An aromatic amine hub is reacted with the dicarboxylic acid intermediate of Example 1, a diamine of the formula: $H_2N-R_3-NH_4$, and an amine end cap in the ratio of 1 mole hub: (w)(m+1) moles intermediate:(w)(m) moles diamine:w moles end cap to form the desired product.

12. Synthesis of Compound (m)

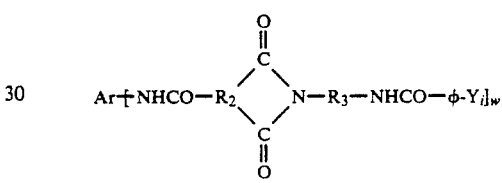

An aromatic amine hub is reacted with an acid halide anhydride of the formula:

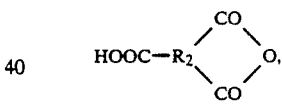

a diamine, and an acid halide end cap in the ratio of 1 mole hub:w moles acid halide anhydride:w moles diamine:w moles end cap to form the desired product. Preferably the reaction occurs in two steps with the reaction

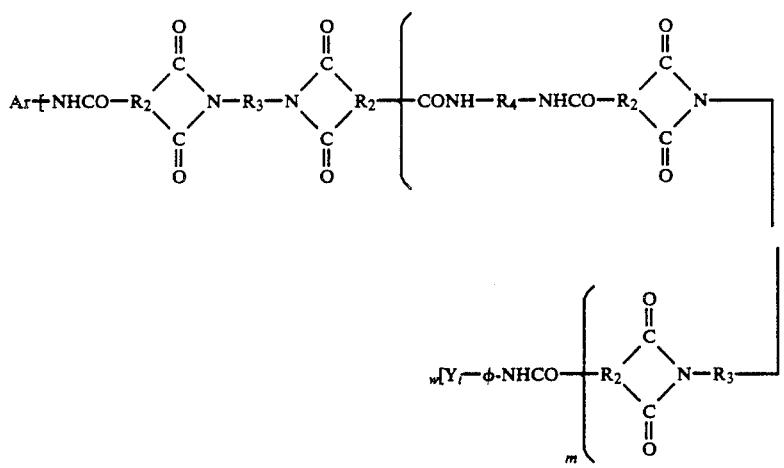

of the hub and acid halide anhydride followed by the addition of the diamine and end cap.

13. Synthesis of Compound (n)

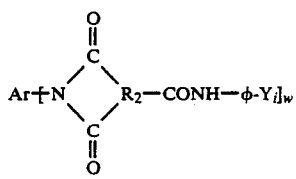

An aromatic amine hub is reacted with an acid anhydride of the formula:

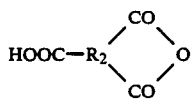

and an amine end cap on the ratio of 1 mole hub:w moles acid anhydride:w moles end cap to form the desired product.

14. Synthesis of Compound (o)

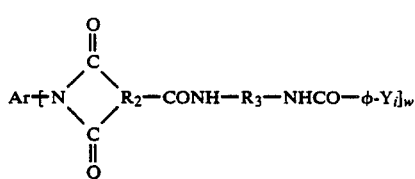

An aromatic amine hub is reacted with the acid anhydride of Example 13, a diamine of the formula $H_2N-R_3-NH_2$, and an acid halide end cap in the ratio of 1 mole hub:w moles acid anhydride:w moles diamine:w moles end cap to yield the desired product. Preferably the reaction occurs in two steps comprising the initial reaction between the hub and the acid anhydride with the subsequent simultaneous addition of the diamine and end cap.

15. Synthesis of Compound (p)

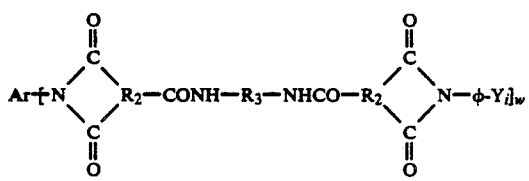

An aromatic amine hub is reacted with an acid anhydride of Example 13, a diamine of the formula $H_2N-R_3-NH_2$, and an amine end cap in the ratio of 1 mole hub:2w moles acid anhydride:w moles diamine:w moles end cap to yield the desired product. Preferably the end cap and half of the acid anhydride are mixed to form an end cap conjugate of the formula:

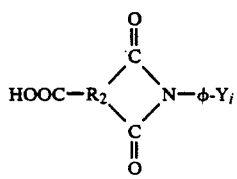

prior to mixing the reactants to form the oligomer. It also may be wise to mix the remaining acid anhydride with the hub to form an intermediate of the formula.

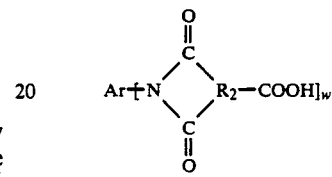

prior to adding the diamine and end cap conjugate.

Alternatively, the product can be made by reacting the hub with dianhydride intermediate of Example 2 and an amine end cap.

16. Synthesis of Compound (q)

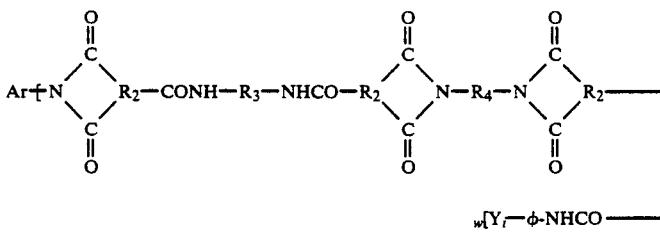

An aromatic amine hub is reacted with the intermediate of Example 2, a diamine of the formula: $H_2N-R_4-NH_2$, and an end cap conjugate formed by reacting an end cap amine with an acid halide anhydride of the formula:

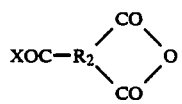

hub:w moles intermediate:w moles end cap conjugate. The conjugate has the formula:

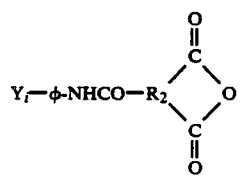

Alternatively, the product can be prepared by reacting the hub with an acid anhydride of the formula:

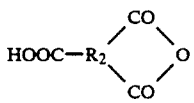

followed by reaction with an amine of the formula $H_2N-R_3-NH_2$, the intermediate of Example 1, and an amine end cap. Stepwise addition of the diamine to the extended hub followed by addition of the intermediate of Example 1 and amine end cap will reduce competitive side reactions.

Synthesis of Compound (r)

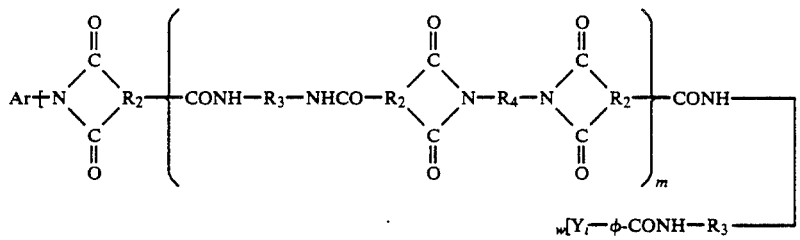

An aromatic amine hub is reacted with an acid anhydride of the formula:

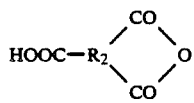

to form an acid hub intermediate which is reacted with a diamine of the formula $H_2N-R_3-NH_2$, a dicarboxylic acid or acid halide intermediate of Example 1, and an acid or acid halide end cap in the ratio of 1 mole hub intermediate (w)(m+1) moles diamine:(w)(m) moles dicarboxylic acid intermediate:w moles end cap to yield the desired Alternatively, the product can be formed by reacting an amine hub with the dianhydride intermediate of Example 2, a diamine of the formula $H_2N-R_3-NH_2$, and acid anhydride of the formula:

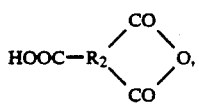

a second diamine of the formula $H_2N-R_3-NH_2$, and an acid halide end cap in a stepwise reaction.

18. Synthesis of Compound (s)

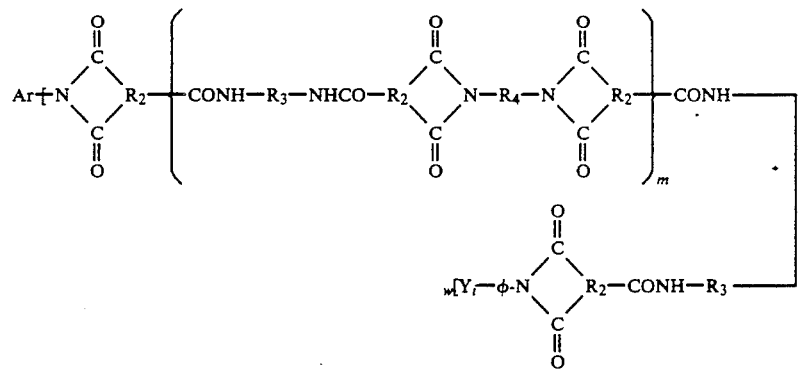

An aromatic amine hub is reacted with the dianhydride intermediate of Example 2, a diamine of the formula $H_2N-R_3-NH_2$, and an amine end cap in the ratio of 1 mole hub:2w moles intermediate:w moles diamine:w moles end cap to yield the desired product.

19. Synthesis of Compound (t)

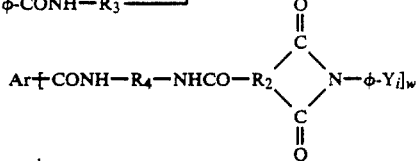

An aromatic acid hub is reacted with a diamine, an acid anhydride, and an amine end cap in the ratio of 1 mole hub: w moles diamine: w moles acid anhydride: w moles end cap to yield the desired product. Preferably the reaction includes the steps of reacting the acid anhydride with the end cap prior to addition of the hub and diamine.

20. Synthesis of Compound (u)

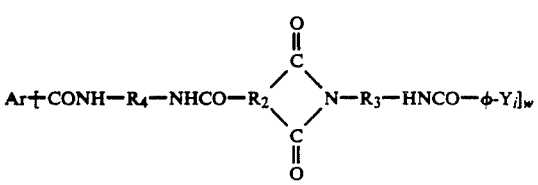

An aromatic acid hub is reacted with a diamine to form an amine extended hub conjugate that is reacted with an acid halide anhydride, another diamine, and an acid halide end cap to yield the desired product. Preparing an end cap conjugate by reacting the second diamine with the end cap prior to the addition of the other reactants reduces side or competitive reactions.

21. Synthesis of Compound (v)

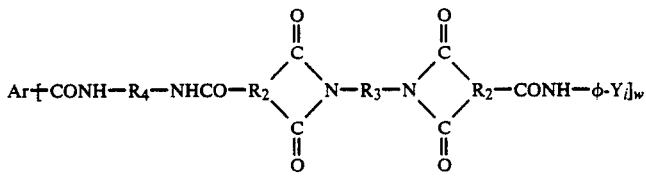

An aromatic acid hub is reacted with a diamine, the intermediate of Example 1, and an amine end cap in the ratio of 1 mole hub:w moles diamine:w moles intermediate:w moles end cap. Preferably, the reaction occurs in two stages with the hub being mixed with the diamine to form an amine conjugate to which the acid or acid halide intermediate and end cap is added simultaneously.

22. Synthesis of Multidimensional Oligomers Using Same Diamine

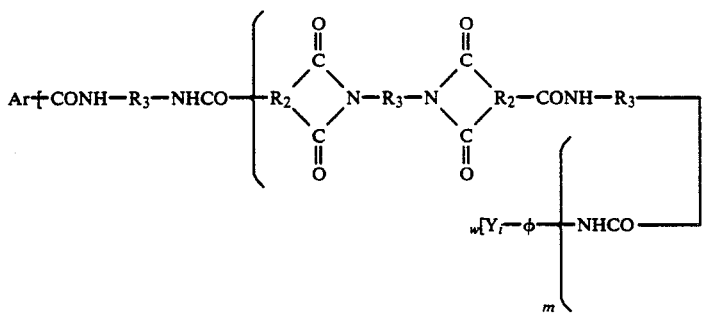

An aromatic acid hub is reacted with a diamine of the formula $H_2N—R_3—NH_2$, the intermediate of Example 1, and an amine cap in the ratio of 1 mole hub:(w)(m+1) moles diamine:(w)(m) moles intermediate:w moles end cap to yield the desire product. The reaction may involve the step of preparing the amine conjugate described in Example 21, and this approach is preferred.

23. Synthesis of Linear Oligomers Using The Same Diamine

Two moles of an amine end cap are reacted with about (m+2) moles of an acid anhydride, such as phthalyl acid anhydride, and about (2m+1) moles of a diamine, such as $H_2N—\phi—SO_2—\phi—O—\phi—SO_2—\phi—NH_2$, to yield the desired product. To avoid side or competitive reactions, it is probably desirable to prepare a dicarboxylic acid intermediate of the formula:

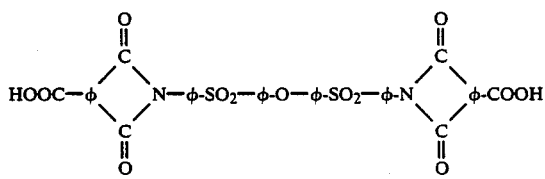

by mixing the acid anhydride and diamine in the ratio of about 2 moles acid anhydride:1 mole diamine prior to adding the remaining reactants for simultaneous condensation to the oligomer.

Comparable oligomers to those described in Examples 1-21 can be prepared by using the same diamine $H_2N—R_3—NH_2$ in the condensation reaction to prepare the intermediate acids or anhydrides and in the oligomeric condensation. That is, in these oligomers, $R_3$ is the same as $R_4$.

24. Synthesis of a Linear Amideimide Polymer

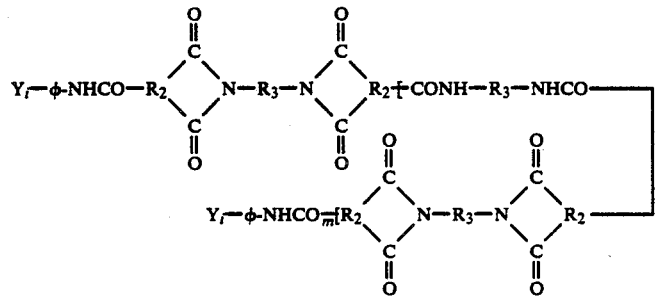

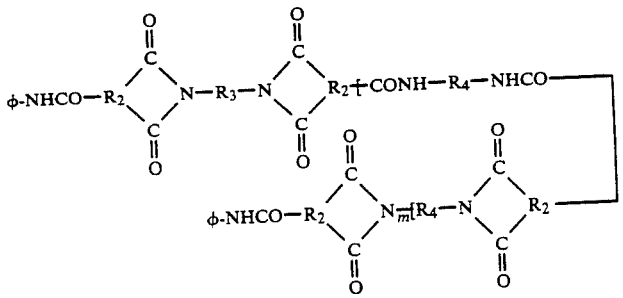

The method of Example 1 is followed except that aniline is substituted for the amine end cap. The product is a comparable polymer of similar formula weight and structure to the oligomer of Example 1 but being incapable of crosslinking because of the lack of crosslinking sites (hydrocarbon unsaturation) in the end caps. The aniline provides MW control and quenches the amideimide condensation.

Comparable noncrosslinking polymers can be obtained according to the methods of Examples 2-23 using aniline, benzoic acid, or similar compounds to quench the syntheses, as will be understood by those of ordinary skill.

25. Preparation of a Blend

Solutions of compound (a) made in accordance with Example 1 and the polymer made in accordance with Example 24 are mixed to prepare a blend solution that can be swept out into fiber reinforcement to form a blended prepreg or that can be dried to recover the blend. The blend generally includes substantially equimolar amounts of the oligomer and polymer, although the ratio can be varied to control the properties of the blend.

Comparable pyrimidine-based oligomers can also be prepared in similar syntheses.

Those skilled in the art will recognize the generality of these reaction schemes in the production of polyamideimide oligomers, blends, prepregs, and advanced composites.

While preferred embodiments have been described, those skilled in the art will readily recognize alterations, variations, and modifications which might be made without departing from the inventive concept. Therefore, the claims should be interpreted liberally with the support of the full range of equivalents known to those of ordinary skill based upon this description. The examples are given to illustrate the invention and not intended to limit it. Accordingly, the claims should only be limited as is necessary in view of the pertinent prior art.

We claim:

1. A polyamideimide oligomer, comprising an oligomer selected from the group consisting of:

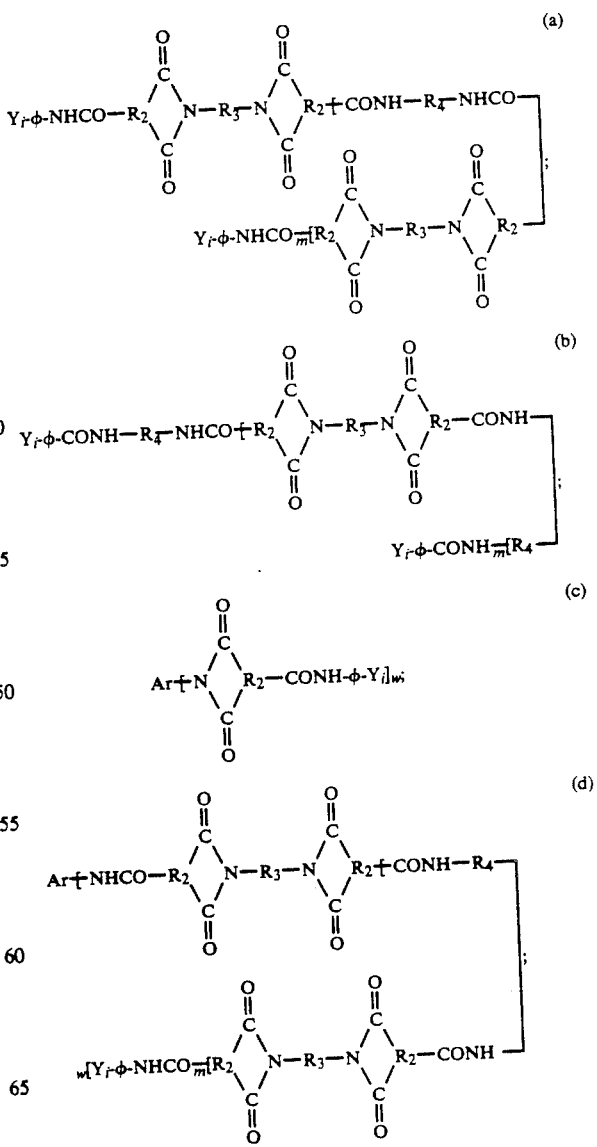

-continued
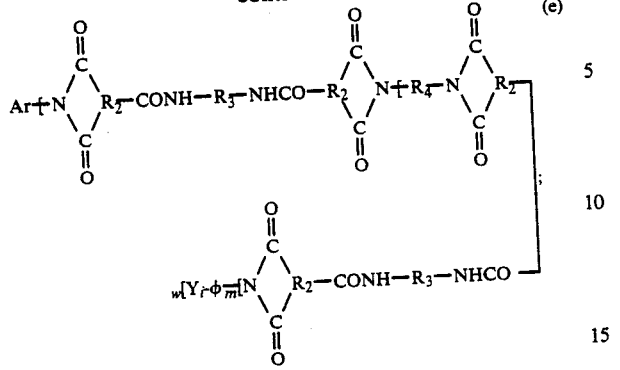 (e)
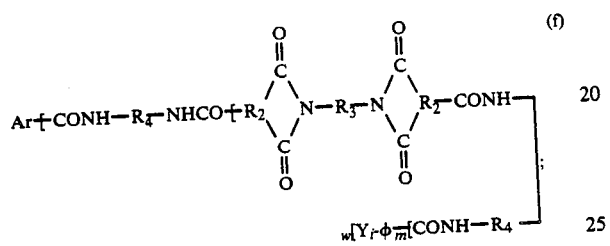 (f)
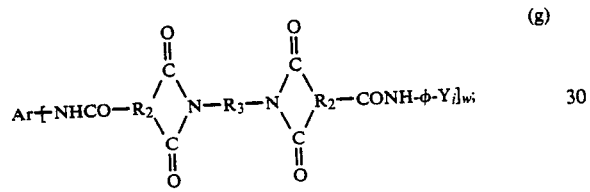 (g)
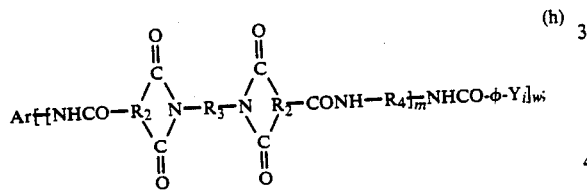 (h)
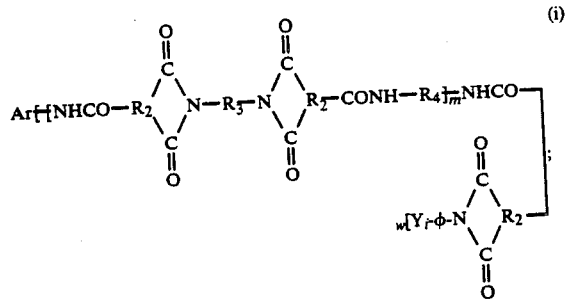 (i)
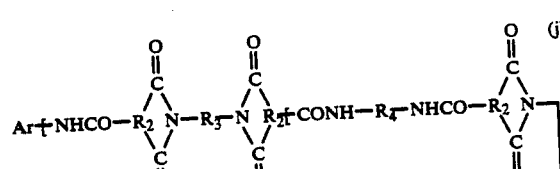 (j)
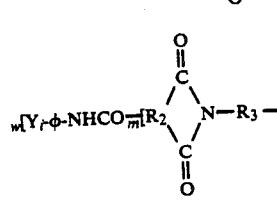
-continued
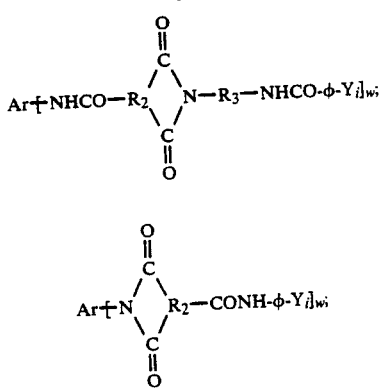 (k)
(l)
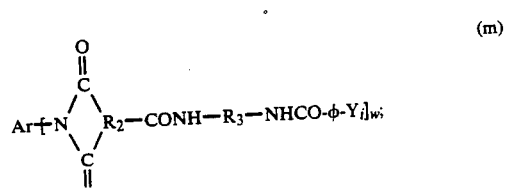 (m)
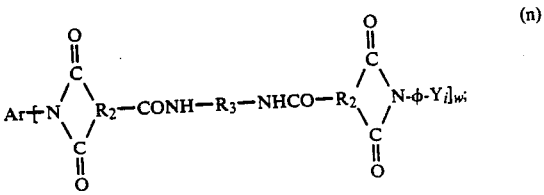 (n)
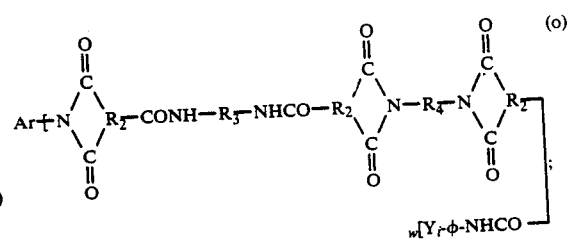 (o)
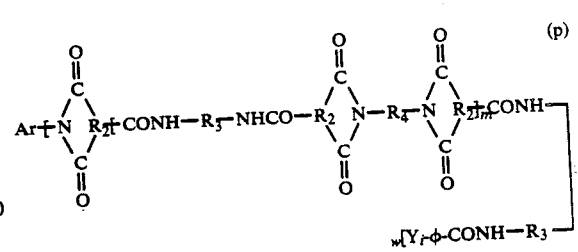 (p)
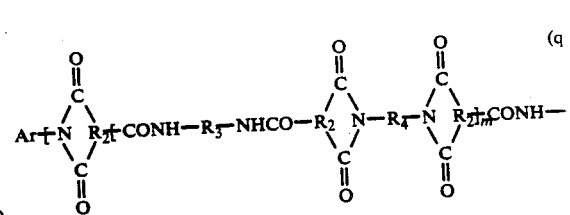 (q)

-continued (r) 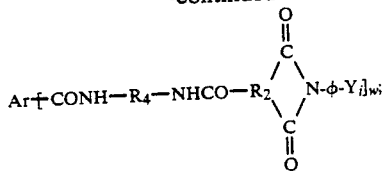

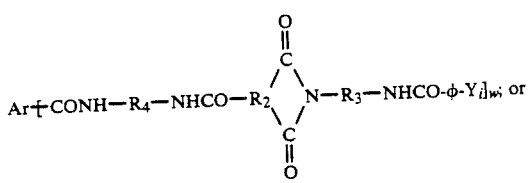

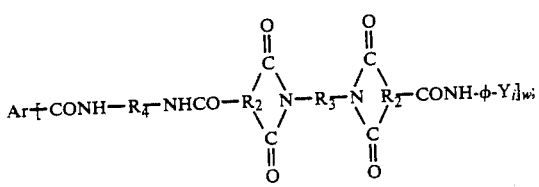

wherein
Y =

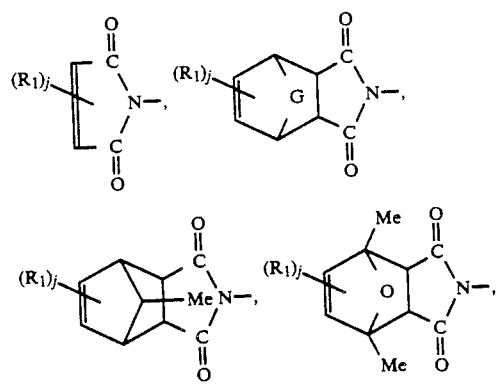

-continued

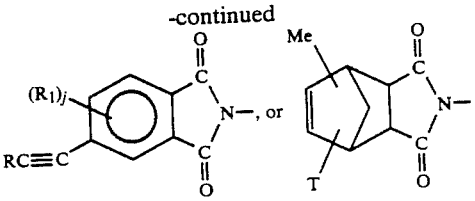 , or wherein
R₁ = lower alkyl, lower alkoxy, aryl, aryloxy, substituted alkyl, substituted aryl, halogen, or mixtures thereof;
j = 0, 1, or 2;
G = —CH₂—, —O—, —S—, —SO₂—, —SO—, —CO—, —CHR—, or —CR₂—;
T = methallyl or allyl;
Me = methyl;
R = hydrogen, lower alkyl, or phenyl;
R₂ = a trivalen organic radical;
R₃ = a divalent organic radical;
R₄ = a divalent organic radical;
m = a small integer;
i = 1 or 2;
Ar = an aromatic radical of valency w; and
w = 3 or 4.

2. The oligomer of claim 1 wherein R₃ is the same as R₄.
3. The oligomer of claim 1 wherein R₂ is phenyl.
4. The oligomer of claim 2 wherein R₃ is phenyl.
5. The oligomer of claim 1 selected from the group consisting of (a), (b), or (c).
6. The oligomer of claim 5 wherein R₂ is phenyl.
7. The oligomer of claim 6 wherein R₃ is the same as R₄.
8. A prepreg comprising the oligomer of claim 1 and a reinforcing additive in fiber or particulate form.
9. A composite comprising a cured oligomer of claim 1.
10. A composite comprising a cured prepreg of claim 8.
11. A polyamideimide oligomer, comprising an oligomer selected from the group consisting of:

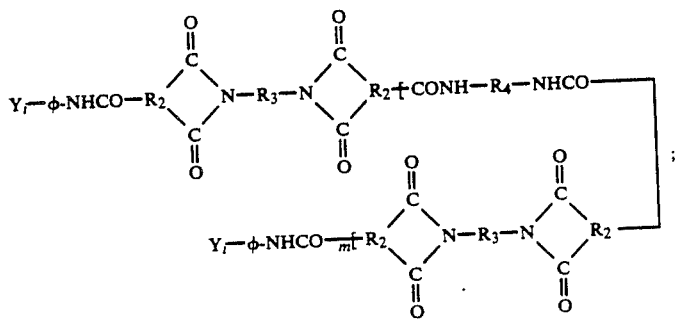

(a)

(b)
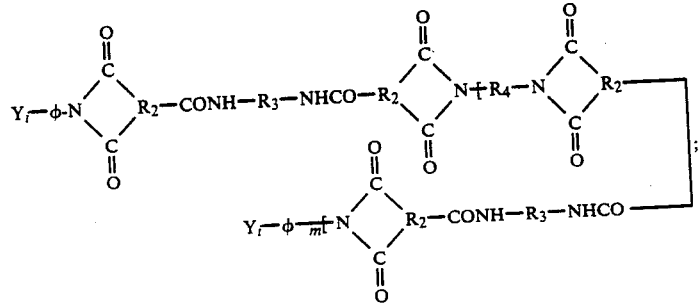
(c)
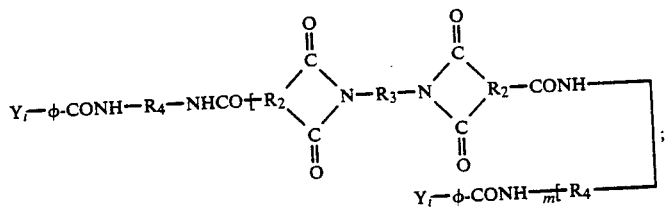
(d)
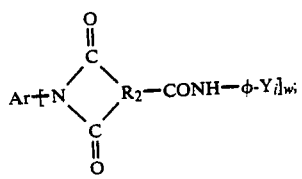
(e)
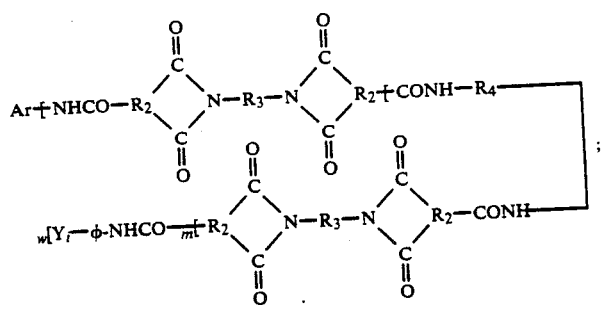
(f)
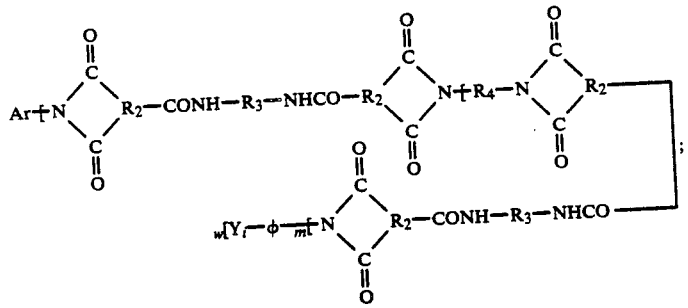
(g)
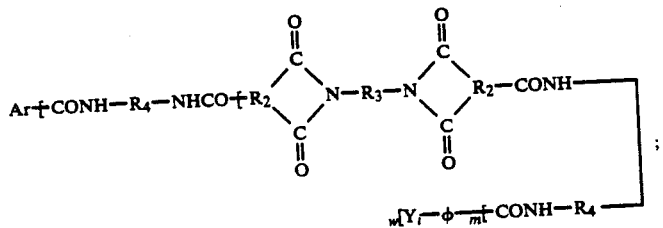

(h)
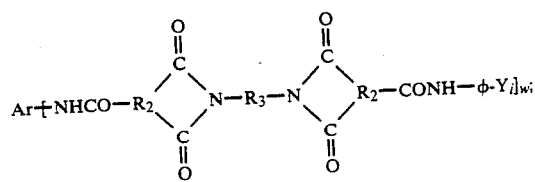
(i)
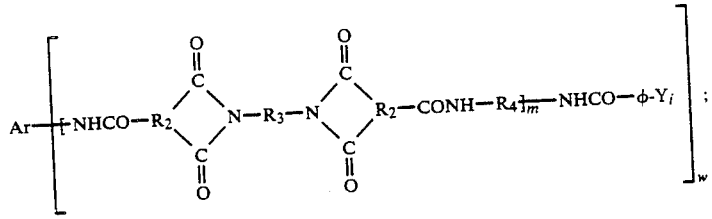
(j)
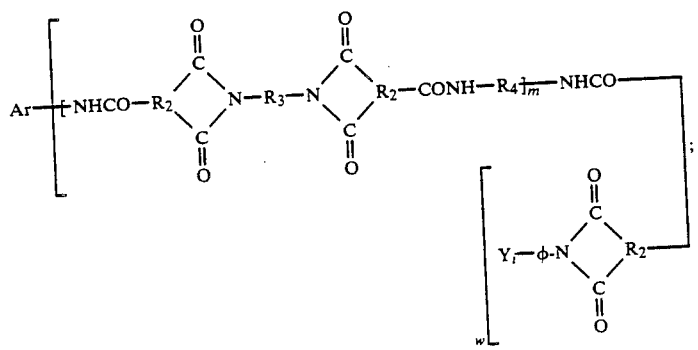
(k)
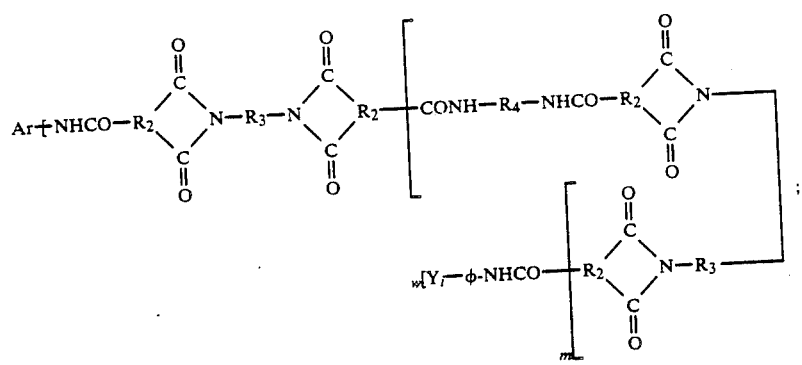
(l)
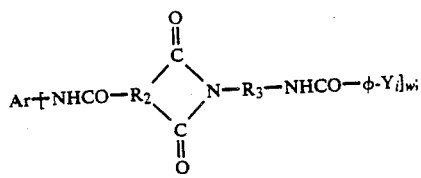
(m)
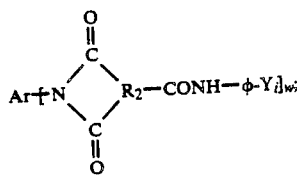
(n)
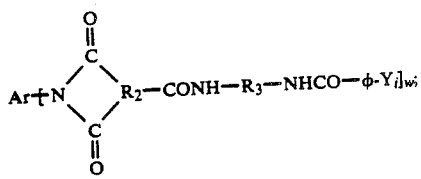

-continued
(o)
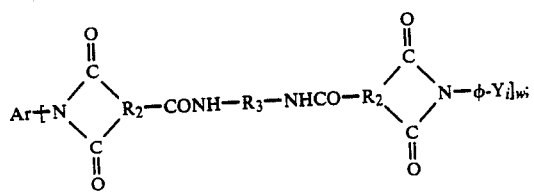
(p)
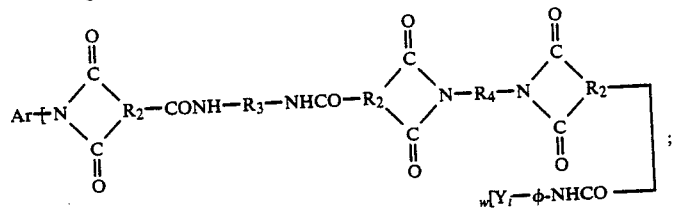
(q)
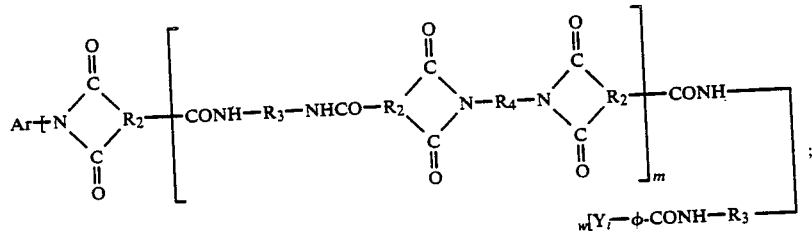
(r)
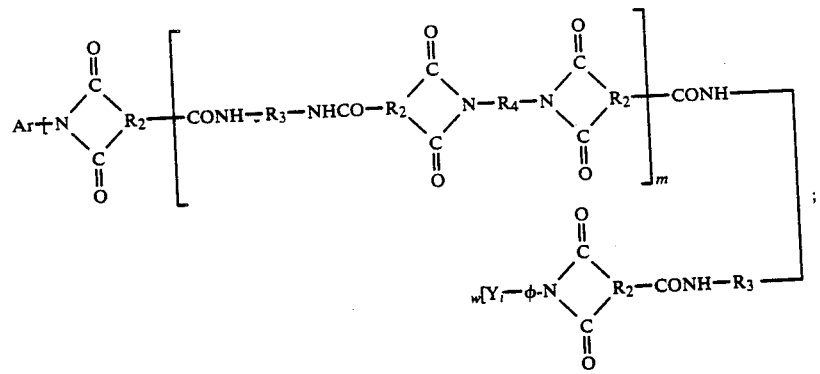
(s)
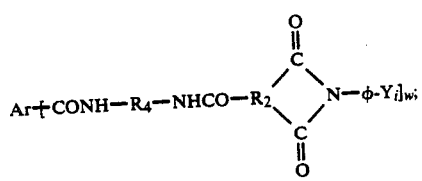
(t)
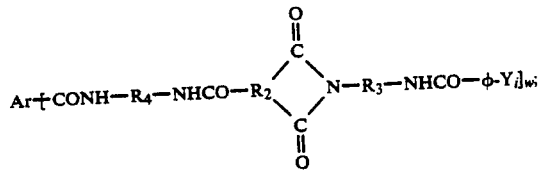
or
(u)
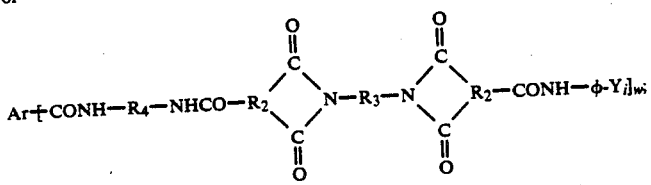
wherein    Y=

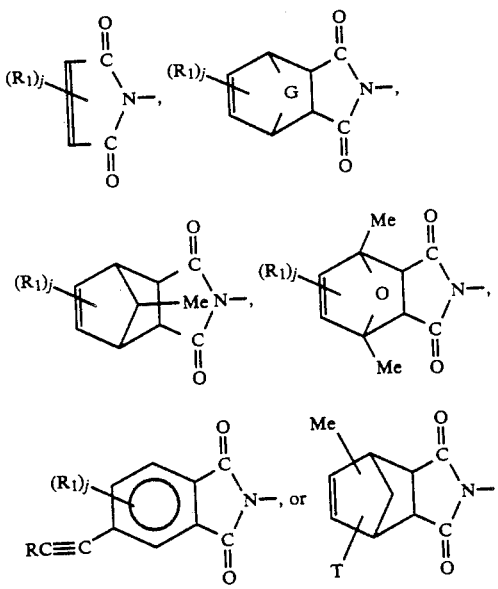

wherein
R₁ = lower alkyl, lower alkoxy, aryl, aryloxy, substituted alkyl, substituted aryl, halogen, or mixtures thereof;
j = 0, 1, or 2;
G = —CH₂—, —O—, —S—, —SO₂—, —SO—, —CO—, —CHR—, or —CR₂—;
T = methallyl or allyl;
Me = methyl;
R = hydrogen, lower alkyl, or phenyl;
R₂ = a trivalent organic radical;
R₃ = a divalent organic radical;
R₄ = a divalent organic radical;
m = a small integer;
i = 2;
Ar = an aromatic radical of valency w; and
w = 3 or 4.

12. The oligomer of claim 11 wherein R₃ is the same as R₄.

13. The oligomer of claim 11 wherein R₂ is phenyl.

14. The oligomer of claim 12 wherein R₃ is phenyl.

15. The oligomer of claim 11 selected from the group consisting of (a), (b), (c), or (d).

16. The oligomer of claim 15 wherein R₂ is phenyl.

17. The oligomer of claim 16 wherein R₃ is the same as R₄.

18. A prepreg comprising the oligomer of claim 11 and a reinforcing additive in fiber or particulate form.

19. A composite comprising a cured oligomer of claim 11.

20. A composite comprising a cured prepreg of claim 18.

21. A method for making a polyamideimide oligomer comprising the steps of:
(a) preparing a dicarboxylic acid intermediate that contains at least two imide linkages along its backbone by condensing an acid anhydride of the formula:

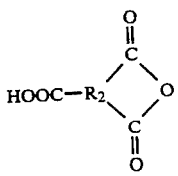

R₂ = a trivalent organic radical, with a diamine; and (b) condensing the intermediate simultaneously with a second diamine and an end cap that is capable of providing at least one crosslinking site to the product, the end cap containing an acid halide or an amine substituent.

22. The method of claim 21 wherein step (b) comprises condensing the intermediate simultaneously with a second diamine and an acid halide end cap.

23. The method of claim 21 wherein the end cap is selected from the group consisting of:

Y$_i$—R*—NH₂ wherein
R* = a phenyl or pyrimidine radical;
i = 1 or 2;
Y =

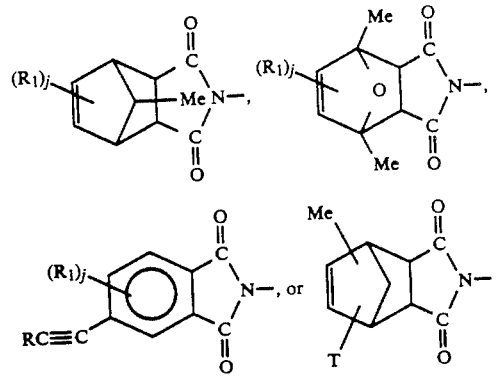

R₁ = lower alkyl, lower alkoxy, aryl, aryloxy, substituted alkyl, substituted aryl, halogen, or mixtures thereof;
j = 0, 1, or 2;
G = —CH₂—, —O—, —S—, —SO₂—, —SO—, —CO—, —CHR—, or —CR₂—;
R = hydrogen, lower alkyl, or phenyl;
T = methallyl or allyl; and
Me = methyl.

24. The method of claim 21 wherein the end cap is selected from the group consisting of:

Y$_i$—R*—COX wherein
R* = a phenyl or pyrimidine radical;

i=1 or 2;
X=halogen;
Y=

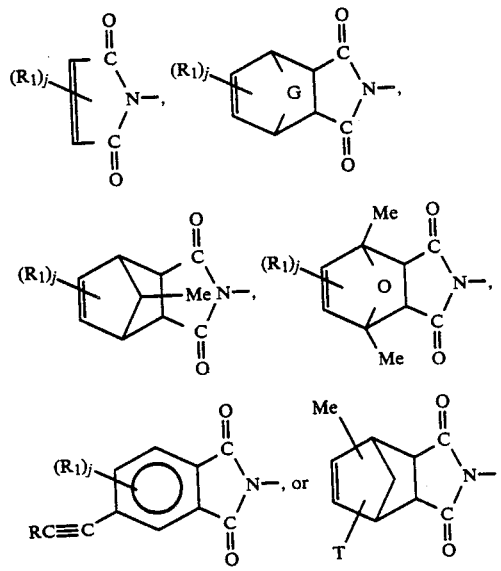

wherein
$R_1$=lower alkyl, lower alkoxy, aryl, aryloxy, substituted alkyl, substituted aryl, halogen, or mixtures thereof;
j=0, 1, or 2;
G=—$CH_2$—, —O—, —S—, —$SO_2$—, —SO—, —CO—, —CHR—, or —$CR_2$—;
R=hydrogen, lower alkyl, or phenyl;
T=methallyl or allyl; and
Me=methyl.

25. A method for making a polyamideimide oligomer comprising the steps of:
(a) preparing a dianhydride intermediate that contains at least two amide linkages along its backbone by condensing an acid halide anhydride of the formula:

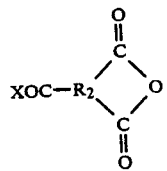

wherein X=halogen and $R_2$=a trivalent organic radical, with a diamine; and
(b) condensing the intermediate simultaneously with a second diamine and an end cap that is capable of providing at least one crosslinking site to the product, the end cap containing an acid halide or an amine substituent.

26. The method of claim 25 wherein step (b) comprises condensing the intermediate simultaneously with a second diamine and an acid halide end cap.

27. The method of claim 25 wherein the end cap is selected from the group consisting of:

wherein $R^*$=a phenyl or pyrimidine radical;
i=1 or 2;
X=halogen;
Y=

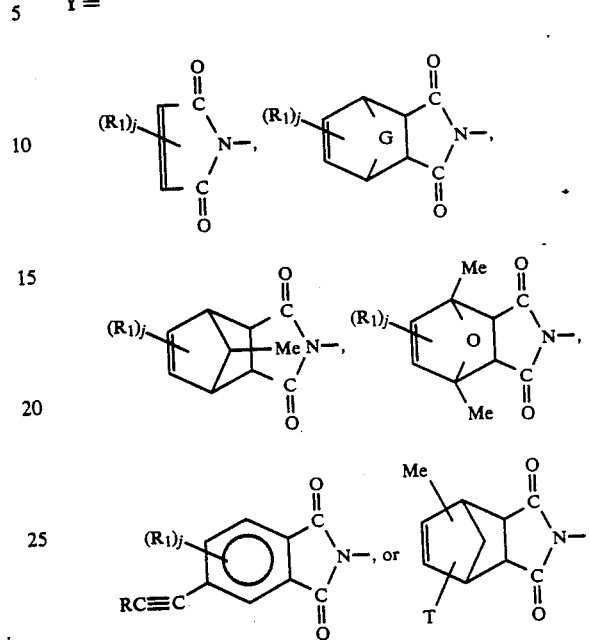

$R_1$=lower alkyl, lower alkoxy, aryl, aryloxy, substituted alkyl, substituted aryl, halogen, or mixtures thereof;
=0, 1, or 2;
G=—$CH_2$—, —O—, —S—, —$SO_2$—, —So—, —CO—, —CHR—, or —$CR_2$—;
R=hydrogen, lower alkyl, or phenyl;
T=methallyl or allyl; and
Me=methyl.

28. The method of claim 25 wherein the end cap is selected from the group consisting of:

$Y_i$—$R^*$—$NH_2$ wherein
$R^*$=a phenyl or pyrimidine radical;
i=1 or 2;
Y=

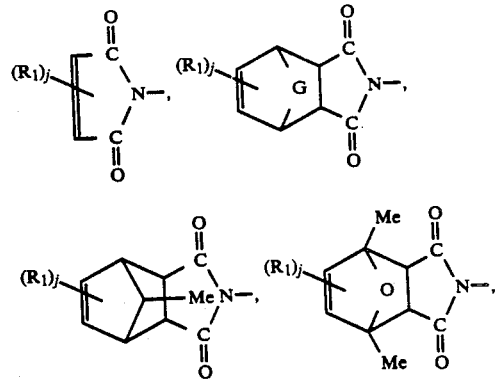

-continued

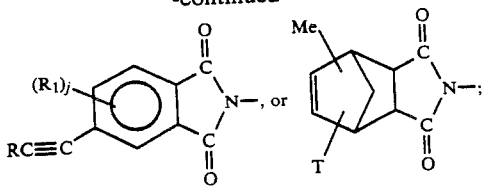

wherein
$R_1$ = lower alkyl, lower alkoxy, aryl, aryloxy, substituted alkyl, substituted aryl, halogen, or mixtures thereof;
j = 0, 1, or 2;
G = —$CH_2$—, —O—, —S—, —$SO_2$—, —SO—, —CO—, —CHR—, or —$CR_2$—;
R = hydrogen, lower alkyl, or phenyl;
T = methallyl or allyl; and
Me = methyl.

29. A method of making a crosslinking polyamideimide oligomer comprising the step of the condensing simultaneously a diamine with an acid anhydride of the formula

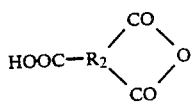

or its acid halide and an end cap selected from the group consisting of $Y_i$—R*—Z wherein
R* = a phenyl or pyrimidine radical;
i = 1 or 2;
Z = —$NH_2$ or

X = halogen;
Y =

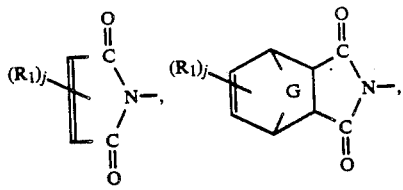

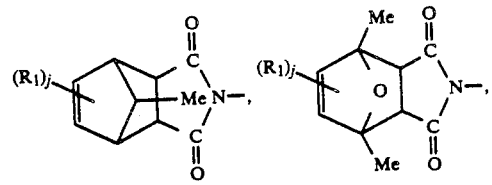

-continued

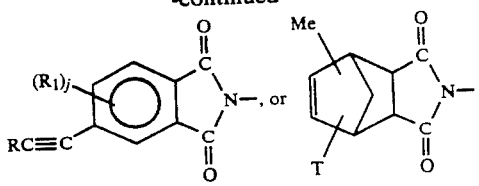

$R_1$ = lower alkyl, lower alkoxy, aryl, aryloxy, substituted alkyl, substituted aryl, halogen, or mixtures thereof;
j = 0, 1, or 2;
G = —$CH_2$—, —O—, —S—, —$SO_2$—, —SO—, —CO—, —CHR—, or —$CR_2$—;
R = hydrogen, lower alkyl, or phenyl;
T = methallyl or allyl; and
Me = methyl.

30. A linear polyamideimide oligomer, comprising a compound of the general formula:

$Y_i$—R*—A—R*—$Y_i$ wherein
i = 2;
A = a divalent radical including at least one segment selected from the group consisting of

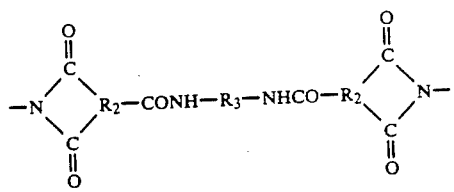

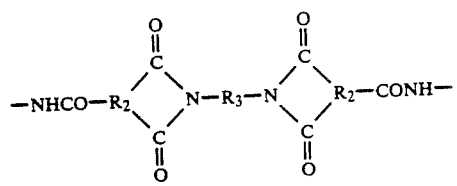

R* = a phenyl or pyrimidine radical;
Y =

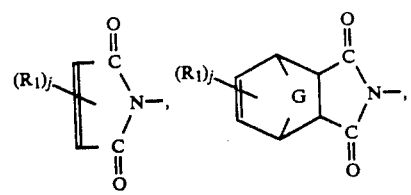

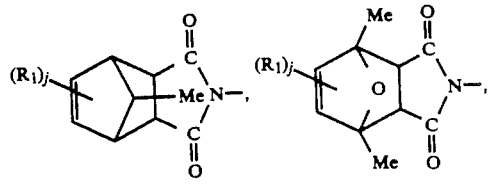

-continued

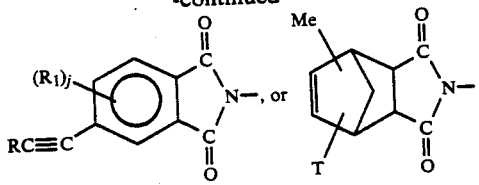

$R_1$ = lower alkyl, lower alkoxy, aryl, aryloxy, substituted alkyl, substituted aryl, halogen, or mixtures thereof;
j = 0, 1, or 2;
G = —$CH_2$—, —O—, —S—, —$SO_2$—, —SO—, —CO—, —CHR—, or —$CR_2$—;
T = methallyl or allyl;
Me = methyl;
R = hydrogen, lower alkyl, or phenyl;
$R_2$ = a trivalent organic radical; and
$R_3$ = a divalent organic radical.

31. The oligomer of claim 30 wherein R* = phenyl.
32. A prepreg comprising the oligomer of claim 30 and a reinforcing additive in fiber or particulate form.
33. A composite comprising a cured oligomer of claim 30.
34. The blend of claim 30 wherein the polymer is an amideimide.
35. A method for making a polyamideimide oligomer comprising the steps of:
  (a) preparing a dicarboxylic acid intermediate that contains at least two imide linkages along its backbone by condensing an acid anhydride of the formula:

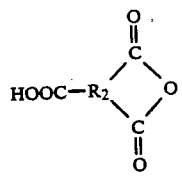

wherein
  $R_2$ = a trivalent organic radical, with a diamine;
  (b) converting the dicarboxylic acid intermediate prepared in step (a) to the corresponding diacid halide; and
  (c) condensing the diacid halide simultaneously with a second diamine and an end cap that is capable of providing at least one crosslinking site to the product, the end cap containing an acid halide or an amine substituent.
36. The method of claim 35 wherein the step (c) comprises condensing the intermediate simultaneously with a second diamine and an acid halide end cap.
37. The method of claim 35 wherein the end cap is selected from the group consisting of:

$Y_i$—R*—$NH_2$ wherein
  R* = a phenyl or pyrimidine radical;
  i = 1 or 2;
  Y =

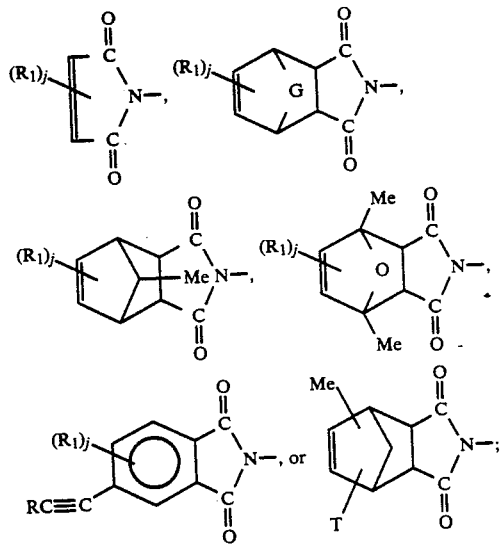

wherein
  $R_1$ = lower alkyl, lower alkoxy, aryl, aryloxy, substituted alkyl, substituted aryl, halogen, or mixtures thereof;
  j = 0, 1, or 2;
  G = —$CH_2$—, —O—, —S—, —$SO_2$—, —SO—, —CO—, —CHR—, or —$CR_2$—;
  R = hydrogen, lower alkyl, or phenyl;
  T = methallyl or allyl; and
  Me = methyl.

38. The method of claim 35 wherein the end cap is selected from the group consisting of:

$Y_i$—R*—COX wherein
  R* = a phenyl or pyrimidine radical;
  i = 1 or 2;
  X = halogen;
  Y =

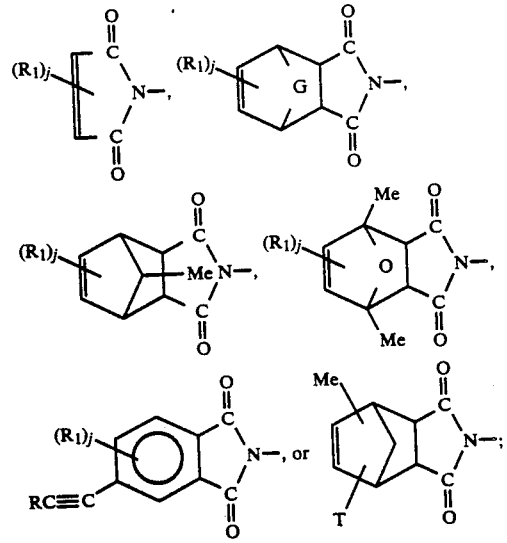

wherein
  $R_1$ = lower alkyl, lower alkoxy, aryl, aryloxy, substituted alkyl, substituted aryl, halogen, or mixtures thereof;
  j = 0, 1, or 2;
  G = —$CH_2$—, —O—, —S—, —$SO_2$—, —SO—, —CO—, —CHR—, or —$CR_2$—;
  R = hydrogen, lower alkyl, or phenyl;
  T = methallyl or allyl; and
  Me = methyl.

* * * * *

UNITED STATES PATENT AND TRADEMARK OFFICE
CERTIFICATE OF CORRECTION

PATENT NO. : 5,104,967

DATED : April 14, 1992

INVENTOR(S) : Clyde H. Sheppard et al.

It is certified that error appears in the above-identified patent and that said Letters Patent is hereby corrected as shown below:

Column 52, claim 1, line 20, "trivalen" should read ---trivalent---.

Column 62, claim 27, line 35, "=0, 1, or 2" should read ---j = 0, 1, or 2---.

Column 62, claim 27, line 36, "So" should read ---SO---.

Signed and Sealed this

Third Day of August, 1993

Attest:

MICHAEL K. KIRK

*Attesting Officer*  *Acting Commissioner of Patents and Trademarks*